United States Patent
Lenz et al.

(10) Patent No.: US 8,278,061 B2
(45) Date of Patent: Oct. 2, 2012

(54) POLYMORPHISMS IN THE EGFR PATHWAY AS MARKERS FOR CANCER TREATMENT

(75) Inventors: Heinz-Josef Lenz, Los Angeles, CA (US); Wu Zhang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 338 days.

(21) Appl. No.: 12/523,517

(22) PCT Filed: Jan. 17, 2008

(86) PCT No.: PCT/US2008/000660
§ 371 (c)(1),
(2), (4) Date: Aug. 10, 2009

(87) PCT Pub. No.: WO2008/088860
PCT Pub. Date: Jul. 24, 2008

(65) Prior Publication Data
US 2010/0172901 A1    Jul. 8, 2010

Related U.S. Application Data

(60) Provisional application No. 60/885,601, filed on Jan. 18, 2007, provisional application No. 60/915,551, filed on May 2, 2007.

(51) Int. Cl.
*G01N 33/574* (2006.01)
(52) U.S. Cl. ...................... 435/7.23; 435/6.14
(58) Field of Classification Search .................. None
See application file for complete search history.

(56) References Cited

U.S. PATENT DOCUMENTS
2006/0115827 A1    6/2006    Lenz

FOREIGN PATENT DOCUMENTS

| WO | WO 2004/011625 A2 | 2/2004 |
|---|---|---|
| WO | WO 2007/103823 A2 | 9/2007 |
| WO | WO 2008/088854 A2 | 7/2008 |
| WO | WO 2008/088860 A2 | 7/2008 |
| WO | WO 2008/088861 A2 | 7/2008 |
| WO | WO 2008/088893 A2 | 7/2008 |
| WO | WO 2008/089465 A2 | 7/2008 |
| WO | WO 2009/140556 A2 | 11/2009 |
| WO | WO 2010/124264 A2 | 10/2010 |

OTHER PUBLICATIONS

Zhang et al, Pharmacogenetics and Genomics, Jul. 2006, 16:475-483.*
Vallbohmer et al, J Clin Oncol, 2005, 23:3536-3644.*
Wong et al, Clin Ther, 2005, 27:684-694.*
Liu et al, Cancer Chemother Pharmacol, 2010, 65:849-861.*
Berlin et al, J Clin Oncol, 2010, 28(15 Suppl):4034.*
Ko et al Invest New Drugs, published online Jun. 1, 2011.*
Gold et al J Thorac Oncol, 2010, 5:1472-1476.*
Lievre, A. et al. (2006) "*KRAS* Mutation Status is Predictive of Response to Cetuximab Therapy in Colorectal Cancer," Cancer Res. 66(8):3992-3995.
Baselga, J. (2005) "Does epidermal growth factor receptor status predict activity of cetuximab in colorectal cancer patients?" Nature Clinical Practice, Oncology 2(5):284-285.
Nagashima, F. et al. (2007) "EGFR, Cox-2, and EGF polymorphisms associated with progression-free survival of EGFR-expressing metastatic colorectal cancer patients treated with single-agent cetuximab (IMCL-0144)," Journal of Clinical Oncology, 2007 ASCO Annual Meeting Proceedings 25(18S):4129.
Zhang, W. et al. (2005) "Genomic Polymorphisms of Angiogenesis Pathway Predict Radiosensitivity in Rectal Cancer," Int. J. Radiation Oncology, Biology, Physics 63(2), 2091:S284.
Lenz, H-J, et al. (2006) "EGFR-Targeted Therapies in Solid Tumors," Retrieved from the internet from: URL: http://www.CancerPublications.com.
Ahmed, F.E. (2005) "Molecular markers that predict response to colon cancer therapy," Expert Rev. Mol. Diagn. 5(3):353-375.
Pander, J. et al. (2007) "Pharmacogenetics of EGFR and VEGF inhibition," Drug Discovery Today 12(23/24):1054-1060.
Weidmann, M.W. et al. (2005) "Molecularly Targeted Therapy for Gastrointestinal Cancer," Current Cancer Drug Targets 5:171-193.
Ning, Y. et al. (2009) "VEGF and VEGFR1 gene expression levels and tumor recurrence in adjuvant colon cancer," ASCO Annual Meeting 2009, Abstract No. 4040.
Yang, D. et al. (2006) "Gene Expression Levels of Epidermal Growth Factor Receptor, Survivin, and Vascular Endothelial Growth Factor as Molecular Markers of Lymph Node Involvement in Patients with Locally Advanced Rectal Cancer," Clinical Colorectal Cancer 6(4):305-311.
Gustavsson, B. et al. (2009) "Molecular determinants of efficacy for 5-FU-based treatments in advanced colorectal cancer: mRNA expression for 18 chemotherapy-related genes," Int. J. Cancer 124:1220-1226.
Lurje, G. et al. (2008) "Polymorphisms in *Cyclooxygenase-2* and *Epidermal Growth Factor Receptor* are Associated with Progression-Free Survival Independent of K-ras in Metastatic Colorectal Cancer Patients Treated with Single-Agent Cetuximab," Clin. Cancer Res. 14(23):7884-7895.
Yan, L. et al. (2005) "Pharmacogenetics and pharmacogenomics in oncology therapeutic antibody development," BioTechniques 39:565-568.

* cited by examiner

*Primary Examiner* — Misook Yu
*Assistant Examiner* — Mark Halvorson
(74) *Attorney, Agent, or Firm* — Foley & Lardner LLP; Antoinette F. Konski; Alex Y. Nie

(57) ABSTRACT

The invention provides compositions and methods for identifying patients for single agent anti-EGFR therapy. The methods comprise determining the genomic polymorphism present in a predetermined region of a gene of interest and correlating the polymorphism to the predictive response. Patients identified as responsive are then treated with the appropriate therapy.

5 Claims, 6 Drawing Sheets

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggaaaatccc agaaattctc gc                                                  22

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caacagcctg actacctatt acgcggg                                             27

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctgaagacac atttttactc ccaam                                               25

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccaaaagcc acactcaaag ac                                                  22

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```

```
aaggaagagg agactctgcg cagagc                                          26

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
taaatgtatg tatgtgggtg ggtgtgtcta cagg                                 34

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catttgcaaa cagaggctca                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtgacagag caaggcaaag                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
accccagggc tctatgggaa                                                 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgagggcaca agaagcccct                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgctgtgacc cactctgtct                                                 20
```

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccagaaggtt gcacttgtcc                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agctttggtt ggttttggtg                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctggaaaca aaaggcattc                                                   20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttgttctaac acctgccact ct                                                22

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcaaacctg agtctcaca                                                    19

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtttgaaatt ttaaagtact tttgat                                            26

<210> SEQ ID NO 18
```

<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttcaaatta ttgtttcatt gc                                            22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
attctggcca tcgccgcttc                                               20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctccttgttt cttggaaaga gacg                                          24

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtgaagttca tttccaatcc gc                                            22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gggacatcac cctcacttac                                               20

POLYMORPHISMS IN THE EGFR PATHWAY AS MARKERS FOR CANCER TREATMENT

CROSS-REFERENCE TO RELATED APPLICATIONS

This application is a national stage application under 35 U.S.C. §371 of International Application No. PCT/US2008/000660, filed Jan. 17, 2008, which in turn claims the benefit under 35 U.S.C. §119(e) of provisional applications U.S. Ser. Nos. 60/885,601, filed on Jan. 18, 2007 and 60/915,551, filed on May 2, 2007. The contents of each of these applications are incorporated by reference into the present disclosure in their entirety.

FIELD OF THE INVENTION

This invention relates to the field of pharmacogenomics and specifically to the application of genetic polymorphism(s) to diagnose and treat diseases.

BACKGROUND OF THE INVENTION

In nature, organisms of the same species usually differ from each other in some aspects, e.g., their appearance. The differences are genetically determined and are referred to as polymorphism. Genetic polymorphism is the occurrence in a population of two or more genetically determined alternative phenotypes due to different alleles. Polymorphism can be observed at the level of the whole individual (phenotype), in variant forms of proteins and blood group substances (biochemical polymorphism), morphological features of chromosomes (chromosomal polymorphism) or at the level of DNA in differences of nucleotides (DNA polymorphism).

Polymorphism also plays a role in determining differences in an individual's response to drugs. Pharmacogenetics and pharmacogenomics are multidisciplinary research efforts to study the relationship between genotype, gene expression profiles, and phenotype, as expressed in variability between individuals in response to or toxicity from drugs. Indeed, it is now known that cancer chemotherapy is limited by the predisposition of specific populations to drug toxicity or poor drug response. For a review of the use of germline polymorphisms in clinical oncology, see Lenz (2004) J. Clin. Oncol. 22(13):2519-2521; Park et al. (2006) Curr. Opin. Pharma. 6(4):337-344; Zhang et al. (2006) Pharma. and Genomics 16(7):475-483 and U.S. Patent Publ. No. 2006/0115827. For a review of the use of pharmacogenomics for the treatment of cancer, see Yan and Beckman (2005) Biotechniques 39:565-568 and Lenz (2006) Pharmacogenomics and Colorectal Cancer, Chpt. 18 in Trends in Cancer for the 21$^{st}$ Century, 2$^{nd}$ Ed., Springer.

Colorectal cancer (CRC) is the second leading lethal malignancy in the United States. In the year 2007, an estimate of 153,760 new cases will be diagnosed and 52,180 people will die from this disease (Jemal et al. (2007) CA Cancer J. Clin. 57:43-66). The current therapeutic options for patients with metastatic CRC (mCRC) are 5-fluorouracil (5-FU) based therapy regimens in combination with irinotecan (CPT-11) or oxaliplatin (de Gramont et al. (2000) J. Clin. Oncol. 18:2938-47; Douillard (2000) Lancet 355:1041-7). Despite recent advances in the chemotherapeutic treatment of mCRC, the 5-year overall survival (OS) still remains relatively poor, with a median survival of 18-21 months (Sargent et al. (2005) J. Clin. Oncol. 23:8664-70; Goldberg et al. (2006) J. Clin. Oncol. 24:4085-91). In recent years a number of new drugs and drug combinations have been evaluated for safety and efficacy in patients with metastatic CRC. Targeted agents such as Cetuximab (monoclonal antibody against the epidermal growth factor receptor) have significantly increased efficacy of chemotherapeutic regimens and have been shown to be active in several human cancers (Cunningham et al. (2004) N. Engl. J. Med. 351:337-45; Saltz et al. (2004) J. Clin. Oncol. 22:1201-8).

One of the most promising targets is the epidermal growth factor receptor (EGFR), a member of the type I receptor tyrosine kinase family. EGFR is overexpressed in a variety of malignancies, including up to 77% of CRC and is associated with tumor progression and poor prognosis (Salomon et al. (1995) Crit. Rev. Oncol. Hematol. 19:183-232; Hemming et al. (1992) J. Surg. Oncol. 51:147-52). Activation of the EGF/EGFR axis triggers multiple signaling pathways that result in endothelial cell proliferation, apoptosis, angiogenesis, and metastasis. Herbst and Shin (2002) Cancer 94:1593-611. Conversely, inhibition of the EGFR pathways with anti-EGFR monoclonal antibodies was reported to block cell cycle progression and induce apoptosis in numerous in vitro and xenograft models (Fan et al. (1993) Cancer Res. 53:4637-42; Karnes et al. (1998) Gastroenterology 114:930-9; Wu et al. (1995) J. Clin. Invest. 95:1897-905). Multiple phase II clinical trials demonstrated that Cetuximab has promising efficacy in patients with mCRC (Cunningham et al. (2004) N. Engl. J. Med. 351:337-45; Saltz et al. (2004) J. Clin. Oncol. 22:1201-8).

The Food and Drug Administration has approved the use of Cetuximab, an antibody to the epidermal growth factor receptor (EGFR), either alone or in combination with irinotecan (also known as CPT-11 or Camptosar®) to treat patients with EGFR-expressing, metastatic CRC, who are either refractory or intolerant to irinotecan-based chemotherapy. One recent study (Zhang et al. (2006) Pharmacogenetics and Genomics 16:475-483) investigated whether polymorphisms in genes of the EGFR signaling pathway are associated with clinical outcome in CRC patients treated with single-agent Cetuximab. The study reported that the cyclin D1 (CCND1) A870G and the EGF A61G polymorphisms may be useful molecular markers for predicting clinical outcome in CRC patients treated with Cetuximab.

Other polymorphisms have been reported to be associated with clinical outcome. Twenty-one (21) polymorphisms in 18 genes involved in the critical pathways of cancer progression (i.e., drug metabolism, tumor microenvironment, cell cycle regulation, and DNA repair) were investigated to determine if they will predict the risk of tumor recurrence in rectal cancer patients treated with chemoradiation (Gordon et al. (2006) Pharmacogenomics 7(1):67-88). However, to the best of Applicant's knowledge, correlation of the polymorphisms identified herein have not been correlated with clinical outcome and treatment with single agent Cetuximab or equivalent thereof.

DESCRIPTION OF THE EMBODIMENTS

This invention provides methods to select the appropriate therapy for patients suffering from a metastatic or non-metastatic gastrointestinal neoplasm or malignant tumor, wherein the appropriate therapy comprises administration of an effective amount of an antibody that targets the Epidermal Growth Factor Receptor (EGFR). Such antibodies include but are not limited to Cetuximab (a/k/a Erubitux®) or a biological equivalent thereof. The method requires detecting the identity of at least one allelic variant of a predetermined gene selected from the group identified in Tables 1 and 2 below.

TABLE 1

Predictive Polymorphisms for Response to Single Agent Anti-EGFR Antibody Therapy

| Allele | Predictive Polymorphism | Measured Response |
| --- | --- | --- |
| EGFR at nt +497 | (G/A) G497A SNP | Increase or Elongation in Progression free survival |
| COX-2 at nt −765 | (C/C) G−765C SNP | Increase or Elongation in Progression free survival or Tumor response |
| COX-2 at nt +8473 | (C/C) T8473C SNP | Increase or Elongation in Progression free survival |
| EGF at nt +61 | (G/G) A61G SNP | Increase or Elongation in Progression free survival or Grade 3-4 Toxicity |

TABLE 2

Predictive Genetic Profiles for Response to Single Agent Anti-EGFR Antibody Therapy

| Allele | Predictive Genetic Profile | Measured Response |
| --- | --- | --- |
| COX-2 at nt +8473<br>FCGR3A at nt +158<br>CCND1 at nt +870 | (T/T) T8473C SNP<br>(F/F or F/V) V158F<br>(G/A or A/A) A870G SNP | Increase or Elongation in Progression free survival |
| COX-2 at nt +8473<br>NRP at 3'UTR<br>FCGR2A at nt +131 | (T/C) T8473C SNP<br>(C/C or C/T) NRP 3'UTR<br>(H/H) H131R | Increase or Elongation in Progression free survival |

This invention also provides methods for treating said patient by administering or delivering an effective amount of an anti-EGFR antibody or a biological equivalent thereof to the patient.

The various embodiments are set forth herein.

In one aspect, the invention is a method for identifying patients likely responsive to single agent anti-EGFR antibody therapy by assaying a suitable patient sample from a human patient suffering from a gastrointestinal tumor or gastrointestinal cancer, for at least one, or alternatively at least two, or alternatively at least three, or alternatively all four polymorphisms identified in Table 1, above. Patients having a genotype selected from polymorphisms of (G/A) G497A SNP for the EGFR allele at nt+497; (C/C) G−765C SNP for the COX-2 allele at nt−765; (C/C) T8473C SNP for the COX-2 allele at nt+8473; and/or (G/G) A61G SNP for the EGF allele at nt+61, are likely to show responsiveness to single agent anti-EGFR therapy such as Cetuximab therapy, wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity. In another aspect, patients having a genetic profile selected from the polymorphisms of (T/T) T8473C SNP for the COX-2 allele at nt+8473; (F/F or FN) V158F for the FCGR3A allele at nt+158; and (G/A or A/A) A870G SNP for the CCND1 allele at nt+870 are likely to show responsiveness to single agent anti-EGFR therapy as measured by increase or elongation in progression free survival. In another aspect, patients having a genetic profile selected from the polymorphisms of (T/C) T8473C SNP for the COX-2 allele at nt+8473; (C/C or C/T) for the NRP allele at the 3'UTR; and (H/H)H131R for the FCGR2A allele at nt+131 are likely to show responsiveness to single agent anti-EGFR therapy as measured by any suitable clinical or sub-clinical increase or elongation in progression free survival.

Further provided is a method to determine whether a patient is likely to experience toxicity when treated with single agent anti-EGFR therapy by assaying a suitable patient sample from a patient suffering from a solid malignant gastrointestinal tumor or gastrointestinal cancer, for (G/G) A61G SNP for the EGF allele at nt±61 wherein patients having G/G genotype are more likely to experience Grade 3-4 toxicity upon treatment with single agent anti-EGFR therapy such as Cetuximab. In another aspect, patients having an (A/A) genotype are less likely to suffer Grade 3-4 toxicity. Patient likely to experience this toxicity may be selected for modified therapy or, additional therapies to accommodate the patient's sensitivities.

Suitable patients for these methods include those suffering from a gastrointestinal tumor, e.g., from rectal cancer, colorectal cancer, metastatic colorectal cancer, colon cancer, gastric cancer, metastatic gastric cancer, lung cancer, non-small cell lung cancer and esophageal cancer. In an alternative aspect, the patient is suffering from colorectal cancer. In a yet further aspect, the patient is suffering from metastatic colorectal cancer.

To practice this method, the sample is a patient sample containing the tumor tissue, normal tissue adjacent to said tumor, normal tissue distal to said tumor or peripheral blood lymphocytes. In one aspect, the method also requires isolating a sample containing the genetic material to be tested; however, it is conceivable that one of skill in the art will be able to analyze and identify genetic polymorphisms in situ at some point in the future. Accordingly, the inventions of this application are not to be limited to requiring isolation of the genetic material prior to analysis.

These methods are not limited by the technique that is used to identify the polymorphism of interest. Suitable methods include but are not limited to the use of hybridization probes, antibodies, primers for PCR analysis and gene chips, slides and software for high throughput analysis. Additional polymorphisms can be assayed and used as negative controls and these are identified in Table 3, below and in the experimental section below.

TABLE 3

Additional Polymorphisms Assayed

| Allele | Polymorphism | Measured Response |
| --- | --- | --- |
| CyclinD1 at nt +870 | A870G | No Correlation |
| FCGR2A at nt +131 | H131R | No Correlation |
| FCGR3A at nt +158 | V158F | No Correlation |
| VEGF at nt +936 | C936T | No Correlation |
| IL-8 at nt −251 | T-251A SNP | No Correlation |
| EGFR at Intron I | CA dinucleotide repeat | No Correlation |
| NRP1 at 3'UTR | C/T SNP | No Correlation |

After a patient has been identified as likely to be responsive to the therapy, the invention also provides administering or delivering an effective amount of anti-EGFR antibody or biologically equivalent thereof to the patient. Methods of administration of pharmaceuticals and biologicals are known in the art and are incorporated herein by reference.

In another aspect, the invention is a method for identifying and selecting a therapy comprising single agent anti-EGFR antibody therapy by assaying a suitable patient sample from a patient suffering from a solid malignant tumor or gastrointestinal cancer, for at least one polymorphism, or alternatively at least two, or alternatively at least three, or yet further all four polymorphisms identified in Table 1, above. Patients who are considered positive responders for further antibody therapy have a genotype selected from (G/A) G497A SNP for the EGFR allele at nt+497; (C/C) G−765C SNP for the COX-2 allele at nt−765; (C/C) T8473C SNP for the COX-2 allele at nt+8473; and/or (G/G) A61G SNP for the EGF allele at nt+61. These patients show responsiveness to single agent anti-EGFR therapy or biologically equivalent thereof, wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity. For patients that are (G/G) A61G SNP for the EGF allele at nt+61, these patients are most likely to experienced Grade 3-4 toxicity. However, these patients may still be selected to receive treatment as they are considered positive responders to single agent anti-EGFR antibody therapy. Suitable patients include those suffering from a non-malignant or a solid malignant tumor such as a gastrointestinal tumor, e.g., from rectal cancer, colorectal cancer, metastatic colorectal cancer, colon cancer, gastric cancer, lung cancer, non-small cell lung cancer and esophageal cancer. In an alternative aspect, the patient is suffering from colorectal cancer. In a yet further aspect, the patient is suffering from metastatic colorectal cancer.

In one embodiment, the invention is a method for identifying and selecting a therapy comprising single agent anti-EGFR antibody therapy by assaying a suitable patient sample from a patient suffering from a solid malignant tumor or gastrointestinal cancer, for at least one or alternatively both genetic profiles identified in Table 2, above. Patients who are considered positive responders for further antibody therapy have a genetic profile comprising either (T/T) for COX-2 T8473C SNP; (F/F or F/V) for FCGR3A V158F; and (G/A or A/A) for CCND1 A870G SNP or (T/C) for COX-2 T8473C SNP; (C/C or C/T) for NRP 3'UTR; and (H/H) for FCGR2A H131R. These patients show responsiveness to single agent anti-EGFR therapy or biologically equivalent thereof, wherein responsiveness is any kind of improvement or positive response either clinical or non-clinical selected from, but not limited to, measurable reduction in tumor size or evidence of disease or disease progression, complete response, partial response, stable disease, increase or elongation of progression free survival, increase or elongation of overall survival, or reduction in toxicity.

To practice this method, the sample is a patient sample containing the tumor tissue, normal tissue adjacent to said tumor, normal tissue distal to said tumor or peripheral blood lymphocytes. These methods are not limited by the technique that is used to identify the polymorphism of interest. Suitable methods include but are not limited to the use of hybridization probes, antibodies, primers for PCR analysis and gene chips, slides and software for high throughput analysis. Additional polymorphisms can be assayed and used as negative controls which include, but are not limited to those identified in Table 3, above.

After a patient has been identified as positive for one or more of the polymorphisms identified in Table 1, the invention may further comprise administering or delivering an effective amount of an anti-EGFR antibody or biologically equivalent thereof, to the patient. Methods of administration of pharmaceuticals and biologicals are known in the art and are incorporated herein by reference.

In one aspect, the method also requires isolating a sample containing the genetic material to be tested; however, it is conceivable that one of skill in the art will be able to analyze and identify genetic polymorphisms in situ at some point in the future. Accordingly, the inventions of this application are not to be limited to requiring isolation of the genetic material prior to analysis.

This invention also provides panel, kit, software and/or gene chip or support for patient sampling and performance of the methods of this invention. The kits contain gene chips, slides, software, probes or primers that can be used to amplify and/or for determining the molecular structure of the polymorphisms identified above. In an alternate embodiment, the kit contains antibodies or other polypeptide binding agents that are useful to identify a polymorphism of Table 1 alone, Table 2 alone, Table 1 and 2 in combination, or further combined with those identified in Table 3. Instructions for sampling and using the materials to carry out the methods or steps of the various embodiments of the invention alone or in combination with instructions for administration of the appropriate therapy are further provided.

In a further aspect, the invention is a method comprising comparing the genotype of a patient against the identified genotypes of Table 1 alone, Table 2 alone, Table 1 and 2 in combination, or further combined with Table 3. Suitable patients for the method are those having a gastrointestinal malignant tumor. If a patient has a genotype matching at least one, or alternatively at least two or, or alternatively at least three, or yet further all four of the genotypes identified in Table 1, then an anti-EGFR antibody such as Cetuximab or a biological equivalent thereof, is administered or delivered to the patient. In another aspect, if a patient has a genotype matching at least one or alternatively both of the genetic profiles identified in Table 2, then an anti-EGFR antibody such as Cetuximab or a biological equivalent thereof, is administered or delivered to the patient. This invention also provides the step of administration or delivery of said therapy to the patient.

This invention also provides for a panel of genetic markers selected from, but not limited to the genetic polymorphisms identified in Tables 1 and 2 alone or in combination with each other or in combination with genetic markers identified in Table 3. The panel comprises probes or primers that can be used to amplify and/or for determining the molecular structure of the polymorphisms identified above. The probes or primers can be attached or supported by a solid phase support such as, but not limited to, a gene chip or microarray. The probes or primers can be detectably labeled. This aspect of the invention is a means to identify the genotype of a patient sample for the genes of interest identified above.

MODES FOR CARRYING OUT THE INVENTION

Figure 1:
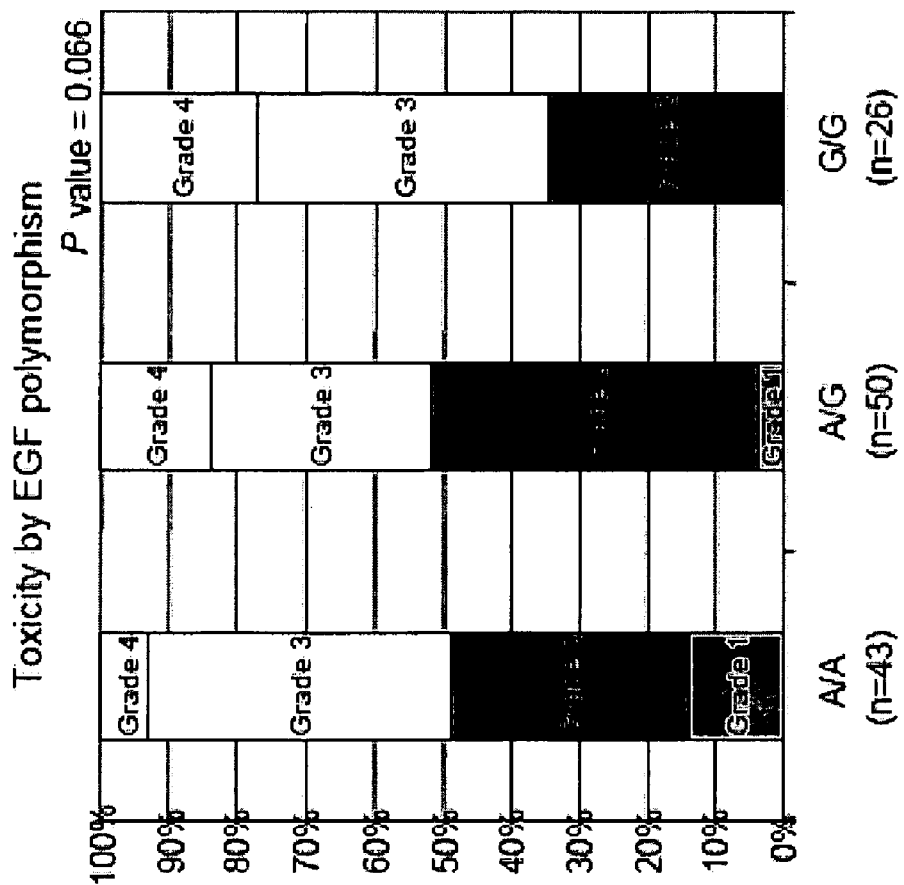
FIG. 1 shows the EGF allele at polymorphism A61G predicts occurrence and grade of toxicity for metastatic colorectal cancer (mCRC) patients treated with Cetuximab. Patients identified as having the genotype G/G are more likely to suffer from Grade 3-4 toxicity, whereas patients identified as having the A/A genotype are less likely to suffer from Grade 3-4 toxicity. The letter n equals the number of patients in each group.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Throughout this disclosure, various publications, patents and published patent specifications are referenced by an identifying citation. The disclosures of these publications, patents and published patent specifications are hereby incorporated by reference in their entirety into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, $3^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney $5^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)); MANIPULATING THE MOUSE EMBRYO: A LABORATORY MANUAL $3^{rd}$ edition (Cold Spring Harbor Laboratory Press, Cold Spring Harbor, N.Y. (2002)).

Definitions

As used herein, certain terms may have the following defined meanings. As used in the specification and claims, the singular form "a," "an" and "the" includes the singular and plural references unless the context clearly dictates otherwise. For example, the term "a cell" includes a single cell and a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method for the stated purpose. "Consisting of" shall mean excluding more than trace elements of other ingredients for claimed compositions and substantial method steps. Embodiments defined by each of these transition terms are within the scope of this invention. It is to be understood that all aspects and embodiments shall include the use of the transition terms "comprising", separately "consisting of" or separately "consisting essentially of."

All numerical designations, e.g., pH, temperature, time, concentration, and molecular weight, including ranges, are approximations which are varied (+) or (-) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

The term "antigen" is well understood in the art and includes substances which are immunogenic. The EGFR is an example of an antigen.

A "native" or "natural" or "wild-type" antigen is a polypeptide, protein or a fragment which contains an epitope and which has been isolated from a natural biological source. It also can specifically bind to an antigen receptor.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention.

The antibodies can be polyclonal or monoclonal and can be isolated from any suitable biological source, e.g., murine, rat, sheep and canine. Additional sources are identified infra.

Cetuximab is an example of an anti-EGFR antibody. It is a chimeric human/mouse monoclonal antibody that targets the epidermal growth factor receptor (EGFR). Biological equivalent antibodies are identified herein as modified antibodies and those which bind to the same epitope of the EGFR antigen and produce a substantially equivalent biological response such as, preventing ligand binding of the EGFR, preventing activation of the EGFR receptor and the blocking of the downstream signaling of the EGFR pathway resulting in disrupted cell growth.

In one aspect, the "biological equivalent" or equivalent is used interchangeably, which means the ability of the antibody to selectively bind its epitope protein or fragment thereof as measured by ELISA or other suitable methods. Biologically equivalent antibodies, include but are not limited to those antibodies, peptides, antibody fragments, antibody variant, antibody derivative and antibody mimetics that bind to the same epitope as the reference antibody.

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')$_2$ fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)) (Bird et al. (1988) Science 242:423-426 and Huston et al. (1988) Proc. Natl. Acad. Sci. USA 85:5879-5883). Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "antibody variant" is intended to include antibodies produced in a species other than a mouse. It also includes antibodies containing post-translational modifications to the linear polypeptide sequence of the antibody or fragment. It further encompasses fully human antibodies.

The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "bispecific molecule" is intended to include any agent, e.g., a protein, peptide, or protein or peptide complex, which has two different binding specificities. The term "multispecific molecule" or "heterospecific molecule" is intended to include any agent, e.g., a protein, peptide, or protein or peptide complex, which has more than two different binding specificities.

The term "heteroantibodies" refers to two or more antibodies, antibody binding fragments (e.g., Fab), derivatives thereof, or antigen binding regions linked together, at least two of which have different specificities.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

A "human monoclonal antibody" refers to antibodies displaying a single binding specificity which have variable and constant regions derived from human germline immunoglobulin sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by heavy chain constant region genes. The IgG isotype consist of four subclasses, IgG1, IgG2, IgG3, and IgG4 each of which having specific activities including the ability to cross into the placenta, act as a complement activator, and to bind to Fc receptors on phahocytic cells. In one embodiment, IgG1 antibodies can cross into the placenta, is the second highest complement activator and has high affinity to bind to Fc receptors on phagocytic cells.

The term "allele", which is used interchangeably herein with "allelic variant", refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The terms "protein", "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "allelic variant of a polymorphic region of the gene of interest" refers to a region of the gene of interest having one of a plurality of nucleotide sequences found in that region of the gene in other individuals.

As used herein, the term "gene of interest" intends one or more genes selected from the group consisting of EGFR, Cox2, EGF, Cyclin D1, FCGR2A, FCGR3A, NRP, VEGF, and IL-8.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e., each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene, whereas the term "phenotype" refers to the detectable outward manifestations of a specific genotype.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "mismatches" refers to hybridized nucleic acid duplexes which are not 100% homologous. The lack of total homology may be due to deletions, insertions, inversions, substitutions or frameshift mutations.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides.

Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine", "cytidine", "guanosine", and "thymidine" are used. It is understood that if the nucleic acid is RNA, a nucleotide having a uracil base is uridine.

The terms "oligonucleotide" or "polynucleotide", or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

As used herein, the term "label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

A "polymorphic gene" refers to a gene having at least one polymorphic region.

The phrase "genetic profile" refers to the identification of a subject's genotype at one or more polymorphisms in one or more genes of interest. The combined composition of the identified polymorphisms comprises a subject's genetic profile. The genetic profile is not limited to the genes and polymorphisms described herein, and can be a part of any number of other polymorphisms, gene expression levels, polypeptide sequences, or any other genetic markers that are unique to the subject or patient.

When a genetic marker or polymorphism "is used as a basis" for selecting a patient for a treatment described herein, the genetic marker or polymorphism is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits. As would be well understood by one in the art, measurement of the genetic marker or polymorphism in a clinical setting is a clear indication that this parameter was used as a basis for initiating, continuing, adjusting and/or ceasing administration of the treatments described herein.

The term "treating" as used herein is intended to encompass curing as well as ameliorating at least one symptom of the condition or disease. For example, in the case of cancer, likely to respond to treatment includes a reduction in cachexia, increase in survival time, elongation in time to tumor progression, reduction in tumor mass, reduction in tumor burden and/or a prolongation in time to tumor metastasis, each as measured by standards set by the National Cancer Institute and the U.S. Food and Drug Administration for the approval of new drugs. See Johnson et al. (2003) J. Clin. Oncol. 21(7):1404-1411.

A "response" implies any kind of improvement or positive response either clinical or non-clinical such as, but not limited to, measurable reduction in tumor size or evidence of disease or disease progression, complete response, partial response, stable disease, increase or elongation of progression free survival, increase or elongation of overall survival, or reduction in toxicity.

The term "likely to respond" shall mean that the patient is more likely than not to exhibit at least one of the described treatment parameters, identified above, as compared to similarly situated patients.

"Progression free survival" (PFS) indicates the length of time during and after treatment that the cancer does not grow. Progression-free survival includes the amount of time patients have experienced a complete response or a partial response, as well as the amount of time patients have experienced stable disease. In one embodiment, the progression free survival is calculated from the time of the first date of treatment until the first observation of disease progression or death from any cause. If a patient has not progressed or died, progression-free survival is censored at the time of the last follow up.

A "complete response" (CR) to a therapy defines patients with evaluable but non-measurable disease, whose tumor and all evidence of disease had disappeared.

A "partial response" (PR) to a therapy defines patients with anything less than complete response were simply categorized as demonstrating partial response. Clinical parameters include those identified above.

"Stable disease" (SD) indicates that the patient is stable.

"Non-response" (NR) to a therapy defines patients whose tumor or evidence of disease has remained constant or has progressed.

"Overall Survival" (OS) intends a prolongation in life expectancy as compared to nave or untreated individuals or patients. In one embodiment, the overall survival time is calculated as the period from the first day of treatment until death from any cause or until death from any cause at which the point data were censored.

"Toxicity" is defined as an adverse event associated with the administration of the drug to the subject. These events include, but are not limited to, asthemia, malaise, somnolence, abdominal pain, fever, pain, infusion reaction, infection, back pain, headache, diarrhea, nausea, vomiting, anorexia, constipation, stomatitis, dyspepsia, leucopenia, anemia, weight loss, peripheral edema, dehydration, insomnia, depression, dyspnea, cough increased, acneform rash, alopecia, skin disorder, nail disorder, preritus, and conjunctivitis. In one embodiment, acneform rash includes an event described as acne, rash, maculopapular rash, pustular rash, dry skin, or exfoliative dermatitis. The severity of these events can be classified by a skilled clinician. Typically, the severity of the toxicity is categorized into one of four grades, i.e. Grade 1, Grade 2, Grade 3, or Grade 4 toxicity or in some aspect combinations thereof.

"Grade 3 Toxicity" is defined as a severe and undesirable adverse event selected from the group consisting of significant symptoms requiring hospitalization or invasive intervention; transfusion; elective interventional radiological procedure; and a therapeutic endoscopy or operation.

"Grade 4 Toxicity" is defined as a life-threatening or disabling adverse event selected from the group consisting of acute, life-threatening metabolic or cardiovascular complications such as circulatory failure, hemorrhage, and sepsis; and a life-threatening physiologic consequences including need for intensive care or an emergent invasive procedure, an emergent interventional radiological procedure, a therapeutic endoscopy, or operation.

"No Correlation" refers to a statistical analysis showing no relationship between the allelic variant of a polymorphic region and clinical parameters.

The term "clinical parameters" refers to a reduction or delay in recurrence of the cancer after the initial therapy, time to tumor progression (TTP), decrease in tumor load or size (tumor response or TR), progression free survival (PF), increase median survival time (OS) or decrease metastases.

Detailed Description of the Embodiments

Until now, there have been only a few clinical and potential molecular markers that identify patients who will most likely benefit from selected anticancer therapies. Recently, mRNA gene expression levels and germline polymorphisms within the EGF/EGFR signaling pathway were tested in the same patient population. Overexpression of VEGF was associated with resistance to Cetuximab, whereas low expression levels of Cox-2, EGFR and IL-8 were significantly associated with improved overall survival (OS) (Vallbohmer et al. (2005) J. Clin. Oncol. 23:3536-44). Furthermore, polymorphisms in Cyclin D1 (CCND1) and Fragment C Gamma Receptors 2A and 3A (FCGR2A and FCGR3A) showed significant associations with OS and PFS, respectively (Zhang et al. (2006) Pharmacogenet Genomics 16:475-83; Zhang et al. (2007) J. Clin. Oncol. 25:3712-8). However, the results of these studies were based on a small number of patients at one institution (n=39). Therefore several positive or negative correlations between the polymorphisms studied and clinical outcome may have been missed. The results reported in this disclosure is a larger, prospective and multi-center study, was aimed to examine whether 11 polymorphisms within 8 genes involved in the EGF/EGFR signaling pathway will serve as molecular markers for Cetuximab response, overall survival and toxicity in mCRC patients treated with single-agent Cetuximab.

Based on the results of these studies, this invention provides a method for selecting a therapeutic regimen or determining if a certain therapeutic regimen is more likely to treat a malignant condition such as cancer or is the appropriate chemotherapy for that patient than other available chemotherapies. In general, a therapy is considered to "treat" cancer if it provides one or more of the following treatment outcomes: reduce or delay recurrence of the cancer after the initial therapy; increase time to tumor progression (TTP), decrease in tumor load or size (tumor response or TR), increase median survival time (OS) or decrease metastases. The method is particularly suited to determining which patients will be responsive or experience a positive treatment outcome with Cetuximab or a biological equivalent thereof. These methods are useful to select therapies for example, highly aggressive cancers such as colorectal cancer or metastatic colon cancer.

In one embodiment, the therapy further comprises adjuvant radiation therapy or other suitable therapy.

The method comprises screening for a genomic polymorphism, genotype, or genetic profile identified in Tables 1, 2 and 3, above.

In one embodiment, the invention is a method for determining whether a human gastrointestinal patient is likely to be responsive to a therapy comprising, or alternatively consisting of, or alternatively consisting essentially of, a single agent anti-EGFR antibody, for example Cetuximab or equivalent thereof, by screening a suitable sample isolated from the patient for at least one genetic polymorphism selected from EGFR G497A SNP, COX-2 G-765C SNP or EGF A61G SNP, wherein for the genetic polymorphism screened, the presence of at least one genetic polymorphism genotype of the group: (G/A) for EGFR G497A SNP; (C/C) for COX-2 G-765C SNP; or (G/G) for EGF A61G SNP indicates the patient is likely responsive to said single-agent anti-EGFR antibody based therapy.

In another embodiment, the invention is a method for determining whether a human gastrointestinal patient is likely to be responsive to a therapy comprising, or alternatively consisting of, or alternatively consisting essentially of, a single agent anti-EGFR antibody, for example Cetuximab or equivalent thereof, by screening a suitable sample isolated from the patient for the genetic polymorphism COX-2 T8473C SNP, wherein for the genetic polymorphism screened, the presence of the genetic polymorphism genotype (C/C) for COX-2 T8473C SNP indicates the patient is likely responsive to said single-agent anti-EGFR antibody based therapy.

In another embodiment, the invention is a method for determining whether a human gastrointestinal patient is likely to be responsive to a therapy comprising, or alternatively consisting of, or alternatively consisting essentially of, a single agent anti-EGFR antibody, for example Cetuximab or equivalent thereof, by screening a suitable sample isolated from the patient for the genetic profile comprising (T/T) for COX-2 T8473C SNP, (F/F or FN) for FCGR3A V158F and (G/A or A/A) for CCND1 A870G SNP, wherein the presence of this genetic profile indicates the patient is likely responsive to said single-agent anti-EGFR antibody based therapy.

In another embodiment, the invention is a method for determining whether a human gastrointestinal patient is likely to be responsive to a therapy comprising, or alternatively consisting of, or alternatively consisting essentially of, a single agent anti-EGFR antibody, for example Cetuximab or equivalent thereof, by screening a suitable sample isolated from the patient for the genetic profile comprising (T/C) for COX-2 T8473C SNP, (C/C or C/T) for NRP 3'UTR and (H/H) for FCGR2A H131R, wherein the presence of this genetic profile indicates the patient is likely responsive to said single-agent anti-EGFR antibody based therapy.

In one aspect of the above embodiments, a patient's form of response to the described therapy is specifically associated with a genetic polymorphism described herein. These associations are described in Tables 1, 2 and 3 and exemplified in the herein described Experimental Examples 1, 2, and 3. For example, a patient identified to have the predictive polymorphism (G/A) for the EGFR (G497A) SNP is likely to have increased or elongated progression free survival in response to administration of an effective amount of an anti-EGFR antibody based therapy.

In a further aspect of the above embodiments, the gastrointestinal cancer is a metastatic or non-metastatic cancer selected from the group consisting of rectal cancer, colorectal cancer, colon cancer, gastric cancer, lung cancer, non-small cell lung cancer and esophageal cancer. In another aspect, the gastrointestinal cancer is metastatic colorectal cancer. In yet another aspect, the human patient is suffering from a cancer selected from the group of recurrent or metastatic squamous cell carcinoma of the head and neck (SCCHN), metastatic squamous cell carcinoma of the penis, colorectal liver metastases, EGFR-positive colorectal cancer, head and neck cancer, pancreas cancer, bladder cancer; or recurrent glioblastoma multiforme.

In another embodiment, the invention is a method for treating a human gastrointestinal cancer patient by administering to the patient an effective amount of a single agent anti-EGFR antibody, for example Cetuximab or an equivalent thereof, based therapy to a patient who is selected for said therapy based on the possession of a genetic polymorphism genotype of the group (G/A) for EGFR G497A SNP; (C/C) for COX-2 G–765C SNP; or (G/G) for EGF A61G SNP.

In another embodiment, the invention is a method for treating a human gastrointestinal cancer patient by administering to the patient an effective amount of a therapy comprising, or alternatively consisting of, or alternatively consisting essentially of, a single agent anti-EGFR antibody, for example Cetuximab or equivalent thereof, to a patient who is selected for said therapy based on the possession of a genetic polymorphism genotype of (C/C) for COX-2 T8473C SNP.

In another embodiment, the invention is a method for treating a human gastrointestinal cancer patient by administering to the patient an effective amount of a therapy comprising, or alternatively consisting of, or alternatively consisting essentially of, a single agent anti-EGFR antibody, for example Cetuximab or equivalent thereof, to a patient who is selected for said therapy based on the possession of a genetic profile of (T/T) for COX-2 T8473C SNP; (F/F or FN) for FCGR3A V158F; and (G/A or A/A) for CCND1 A870G SNP.

In another embodiment, the invention is a method for treating a human gastrointestinal cancer patient by administering to the patient an effective amount of a therapy comprising, or alternatively consisting of, or alternatively consisting essentially of, a single agent anti-EGFR antibody, for example Cetuximab or equivalent thereof, to a patient who is selected for said therapy based on the possession of a genetic profile of (T/C) for COX-2 T8473C SNP; (C/C or C/T) for NRP 3'UTR; and (H/H) for FCGR2A H131R.

In a further aspect of the above methods of treating a human patient, the gastrointestinal cancer is a metastatic or non-metastatic cancer selected from the group consisting of rectal cancer, colorectal cancer, colon cancer, gastric cancer, lung cancer, non-small cell lung cancer and esophageal cancer. In another aspect, the gastrointestinal cancer is metastatic colorectal cancer. In yet another aspect, the human patient is suffering from a cancer selected from the group of recurrent or metastatic squamous cell carcinoma of the head and neck (SCCHN), metastatic squamous cell carcinoma of the penis, colorectal liver metastases, EGFR-positive colorectal cancer, head and neck cancer, pancreas cancer, bladder cancer; or recurrent glioblastoma multiforme.

In another embodiment, the invention is a method for determining whether a human gastrointestinal cancer patient is likely to suffer toxicity associated with the administration of a therapy comprising, or alternatively consisting of, or alternatively consisting essentially of, a single agent anti-EGFR antibody, for example Cetuximab or equivalent thereof, by screening a suitable sample isolated from the patient for the genetic polymorphism of (G/G) for EGF A61G SNP, wherein the presence of the genetic polymorphism indicates that the patient is likely to suffer toxicity. In a further aspect, toxicity includes Grade 1, Grade 2, Grade 3, or Grade 4 toxicity. In yet a further aspect, the patient identified in the above embodiment is more likely to suffer Grade 3 to Grade 4 toxicity.

In another embodiment, the invention is a method for determining whether a human gastrointestinal cancer patient is likely to suffer toxicity associated with the administration of a therapy comprising, or alternatively consisting of, or alternatively consisting essentially of, a single agent anti-EGFR antibody, for example Cetuximab or equivalent thereof, by screening a suitable sample isolated from the patient for the genetic polymorphism of (A/A) for EGF A61G SNP, wherein the presence of the genetic polymorphism indicates that the patient is least likely to suffer toxicity. In a further aspect, toxicity includes Grade 1, Grade 2, Grade 3, or Grade 4 toxicity. In yet a further aspect, the patient identified in the above embodiment is least likely to suffer Grade 3 to Grade 4 toxicity.

In another embodiment, the invention provides for a panel of genetic markers for determining whether a patient is likely responsive to a single agent anti-EGFR, for example Cetuximab or an equivalent thereof, based therapy. In one aspect the panel comprises a group of primers and/or probes that identify the genetic markers of the group EGFR G497A SNP, COX-2 G–765C SNP, EGF A61G SNP, COX-2 T8473C SNP, FCGR3A V158F, CCND1 A870G SNP, NRP 3'UTR or FCGR2A H131R.

In addition to the method exemplified herein, the EGFR polymorphism (G+497A) can be identified by known methods such as those described in Baselga (2005) Nature Clinical Practice Oncology 2:284-285. Identification of the genotype FCGR2A H+131R is described in Cheung et al. (2006) J. Clin. Oncl. 24(18):2885-2890. CCND1 (Cyclin D1) polymorphism (A+870G) is identified by known methods such as those disclosed in Zhang et al. (2006) J. Clin. Oncol. 22(145): 3518. Identification of the genotype FCGR3A+158 F/F or V/F genotype is described in Yan and Beckman (2005) Bio-Techniques 39:565-568. Methods for identification of the Cox-2 genotype G–765C is described in Pereira et al., (2006) World J. Gastroenterol 12:5473-5478 and EGF genotype A+61G is described in Goto et al. (2005) Cancer Epidemiol. Biomarkers Prey. 14:2454-2456. The VEGF allele with C+936T polymorphism is identified and described in Zhang et al. (2006) Pharmacogenet Genomics 7:475-483. The IL-8 T-251A allele is identified and described in Zhang et al. (2005) Clin. Colorectal Cancer 5:124-134. Additional methods known and used by Applicant are described in U.S. Patent Publ. Nos. 2006/0115827 and 2006/0094012.

Diagnostic Methods

The invention further provides diagnostic and prognostic methods, which are based, at least in part, on determination of the identity of the polymorphic region of the alleles identified in Tables 1, 2 and 3, above.

For example, information obtained using the diagnostic assays described herein is useful for determining if a subject will likely respond to cancer treatment of a given type or experience toxicity to the treatment. Based on the prognostic information, a doctor can recommend a therapeutic protocol, useful for treating reducing the malignant mass or tumor in the patient or treat cancer in the individual or adjusting that therapy to accommodate the patient's sensitivities.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. Expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Detection of point mutations or additional base pair repeats can be accomplished by molecular cloning of the specified allele and subsequent sequencing of that allele using techniques known in the art. Alternatively, the gene sequences can be amplified directly from a genomic DNA preparation from the tumor tissue using PCR, and the sequence composition is determined from the amplified product. As described more fully below, numerous methods are available for analyzing a subject's DNA for mutations at a given genetic locus such as the gene of interest.

A detection method is allele specific hybridization using probes overlapping the polymorphic site and having about 5, or alternatively 10, or alternatively 20, or alternatively 25, or alternatively 30 nucleotides around the polymorphic region. In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described, e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert (1997) Proc. Natl. Acad. Sci. USA 74:560 or Sanger et al. (1977) Proc. Nat. Acad. Sci. 74:5463. It is also contemplated that any of a variety of automated sequencing procedures can be utilized when performing the subject assays (Biotechniques (1995) 19:448), including sequencing by mass spectrometry (see, for example, U.S. Pat. No. 5,547,835 and International Patent Application Publication Number WO94/16101, entitled DNA Sequencing by Mass Spectrometry by H. Koster; U.S. Pat. No. 5,547,835 and international patent application Publication Number WO 94/21822 entitled "DNA Sequencing by Mass Spectrometry Via Exonuclease Degradation" by H. Koster; U.S. Pat. No. 5,605,798 and International Patent Application No. PCT/US96/03651 entitled DNA Diagnostics Based on Mass Spectrometry by H. Koster; Cohen et al. (1996) Adv. Chromat. 36:127-162; and Griffin et al. (1993) Appl. Biochem. Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA Sequencing Employing A Mixed DNA-Polymer Chain Probe" and U.S. Pat. No. 5,571,676 entitled "Method For Mismatch-Directed In Vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249, Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility are used to identify the particular allelic variant. For example, single strand conformation polymorphism (SSCP) may be used to detect differences in electrophoretic mobility between mutant and wild type nucleic acids (Orita et al. (1989) Proc Natl. Acad. Sci. USA 86:2766; Cotton (1993) Mutat. Res. 285:125-144 and Hayashi (1992) Genet. Anal. Tech. Appl. 9:73-79). Single-stranded DNA fragments of sample and control nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 by of high-melting GC-rich DNA by PCR. In a further embodiment, a temperature gradient is used in place of a denaturing agent gradient to identify differences in the mobility of control and sample DNA (Rosenbaum and Reissner (1987) Biophys. Chem. 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci. USA 86:6230 and Wallace et al. (1979) Nucl. Acids Res. 6:3543). Such allele specific oligonucleotide hybridization techniques may be used for the detection of the nucleotide changes in the polymorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell. Probes 6:1).

In another embodiment, identification of the allelic variant is carried out using an oligonucleotide ligation assay (OLA), as described, e.g., in U.S. Pat. No. 4,998,617 and in Landegren et al. (1988) Science 241:1077-1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson et al. (1990) Proc. Natl. Acad. Sci. (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in To be et al. (1996) Nucleic Acids Res. 24: 3728, OLA combined with PCR permits typing of two alleles in a single microtiter well. By marking each of the allele-specific primers with a unique hapten, i.e., digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting the single nucleotide polymorphism in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen et al. (French Patent 2,650, 840; PCT Appln. No. WO91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO91/02087) the method of Goelet, P. et al., supra, is preferably a heterogeneous phase assay, in which the primer or the target molecule is immobilized to a solid phase.

Recently, several primer-guided nucleotide incorporation procedures for assaying polymorphic sites in DNA have been described (Komher et al. (1989) Nucl. Acids. Res. 17:7779-7784; Sokolov (1990) Nucl. Acids Res. 18:3671; Syvanen et al. (1990) Genomics 8:684-692; Kuppuswamy et al. (1991) Proc. Natl. Acad. Sci. (U.S.A.) 88:1143-1147; Prezant et al. (1992) Hum. Mutat. 1:159-164; Ugozzoli et al. (1992) GATA 9:107-112; Nyren et al. (1993) Anal. Biochem. 208:171-175).

These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen et al. (1993) Amer. J. Hum. Genet. 52:46-59).

If the polymorphic region is located in the coding region of the gene of interest, yet other methods than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

Antibodies directed against wild type or mutant peptides encoded by the allelic variants of the gene of interest may also be used in disease diagnostics and prognostics. Such diagnostic methods, may be used to detect abnormalities in the level of expression of the peptide, or abnormalities in the structure and/or tissue, cellular, or subcellular location of the peptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook and Russell, (2001) supra. The protein detection and isolation methods employed herein can also be such as those described in Harlow and Lane, (1999) supra. This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of the peptides or their allelic variants. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the subject polypeptide, but also its distribution in the examined tissue. Using the present invention, one of ordinary skill will readily perceive that any of a wide variety of histological methods (such as staining procedures) can be modified in order to achieve such in situ detection.

In one aspect the invention provided for a panel of genetic markers selected from, but not limited to the genetic polymorphisms above. The panel comprises probes or primers that can be used to amplify and/or for determining the molecular structure of the polymorphisms identified above. The probes or primers can be attached or supported by a solid phase support such as, but not limited to a gene chip or microarray. The probes or primers can be detectably labeled. This aspect of the invention is a means to identify the genotype of a patient sample for the genes of interest identified above. In one aspect, the methods of the invention provided for a means of using the panel to identify or screen patient samples for the presence of the genetic marker identified herein. In one aspect, the various types of panels provided by the invention include, but are not limited to, those described herein. In one aspect, the panel contains the above identified probes or primers as wells as other, probes or primers. In an alternative aspect, the panel includes one or more of the above noted probes or primers and others. In a further aspect, the panel consist only of the above-noted probes or primers.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject has or is at risk of developing disease such as colorectal cancer.

Sample nucleic acid for use in the above-described diagnostic and prognostic methods can be obtained from any cell type or tissue of a subject. For example, a subject's bodily fluid (e.g., blood) can be obtained by known techniques (e.g., venipuncture). Alternatively, nucleic acid tests can be performed on dry samples (e.g., hair or skin). Fetal nucleic acid samples can be obtained from maternal blood as described in International Patent Application No. WO91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo (1992) "PCR In Situ Hybridization: Protocols And Applications", Raven Press, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook and Russell (2001) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi and Kramer (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis (1998) Science 279:1228-9) as has the use of multiple beacons simultaneously (Marras (1999) Genet. Anal. 14:151-6). A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

Labeled probes also can be used in conjunction with amplification of a polymorphism. (Holland et al. (1991) Proc. Natl. Acad. Sci. 88:7276-7280). U.S. Pat. No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Tag-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule—quencher molecule pair that specifically anneals to a region of a target polynucleotide containing the polymorphism.

Probes can be affixed to surfaces for use as "gene chips" or "microarray." Such gene chips or microarrays can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659.

A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarray" and similar technologies are known in the art. Examples of such include, but are not limited to LabCard (ACLARA Bio Sciences Inc.); GeneChip (Affymetrix, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.) a thermal jet spotting system (Hewlett Packard Company); Hyseq HyChip (Hyseq, Inc.); BeadArray (Illumina, Inc.); GEM (Incyte Microarray Systems); a high-throughput microarraying system that can dispense from 12 to 64 spots onto multiple glass slides (Intelligent Bio-Instruments); Molecular Biology Workstation and NanoChip (Nanogen, Inc.); a microfluidic glass chip (Orchid biosciences, Inc.); BioChip Arrayer with four PiezoTip piezoelectric drop-on-demand tips (Packard Instruments, Inc.); FlexJet (Rosetta lnpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "Gene chips" or a "microarray" are also described in US Patent Publ. Nos.: 2007-0111322, 2007-0099198, 2007-0084997, 2007-0059769 and 2007-0059765 and US Pat. Nos. 7,138,506, 7,070,740, and 6,989,267.

In one aspect, "gene chips" or "microarrays" containing probes or primers for genes of Tables 1, 2 and 3 alone or in combination are prepared. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers may be detectably labeled thereby identifying the polymorphism in the gene(s) of interest. Alternatively, a chemical or biological reaction may be used to identify the probes or primers which hybridized with the DNA or RNA of the gene(s) of interest. The genotypes of the patient is then determined with the aid of the aforementioned apparatus and methods.

Nucleic Acids

In one aspect, the nucleic acid sequences of the gene's allelic variants, or portions thereof, can be the basis for probes or primers, e.g., in methods for determining the identity of the allelic variant of the FCGR3A 158 polymorphic region(s). Thus, they can be used in the methods of the invention to determine which therapy is most likely to treat an individual's cancer.

The methods of the invention can use nucleic acids isolated from vertebrates. In one aspect, the vertebrate nucleic acids are mammalian nucleic acids. In a further aspect, the nucleic acids used in the methods of the invention are human nucleic acids.

Primers for use in the methods of the invention are nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes for use in the methods of the invention are nucleic acids which hybridize to the region of interest and which are not further extended. For example, a probe is a nucleic acid which hybridizes to the polymorphic region of the gene of interest, and which by hybridization or absence of hybridization to the DNA of a subject will be indicative of the identity of the allelic variant of the polymorphic region of the gene of interest.

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of the gene of interest.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

Yet other preferred primers of the invention are nucleic acids which are capable of selectively hybridizing to an allelic variant of a polymorphic region of the gene of interest. Thus, such primers can be specific for the gene of interest sequence, so long as they have a nucleotide sequence which is capable of hybridizing to the gene of interest.

The probe or primer may further comprises a label attached thereto, which, e.g., is capable of being detected, e.g., the label group is selected from amongst radioisotopes, fluorescent compounds, enzymes, and enzyme co-factors.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

The nucleic acids used in the methods of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane. See, e.g., Letsinger et al. (1989) Proc. Natl. Acad. Sci. U.S.A. 86:6553-6556; Lemaitre et al. (1987) Proc. Natl. Acad. Sci. 84:648-652; and PCT Publication No. WO 88/09810, published Dec. 15, 1988), hybridization-triggered cleavage agents, (see, e.g., Krol et al. (1988) BioTechniques 6:958-976) or intercalating agents (see, e.g., Zon (1988) Pharm. Res. 5:539-549. To this end, the nucleic acid used in the methods of the invention may be conjugated to another molecule, e.g., a peptide, hybridization triggered cross-linking agent, transport agent, hybridization-triggered cleavage agent, etc.

The isolated nucleic acids used in the methods of the invention can also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof, to be used in the methods of the invention can be prepared according to methods known in the art and described, e.g., in Sambrook and Russell (2001) supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above).

Oligonucleotides can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports. Sarin et al. (1988) Proc. Natl. Acad. Sci. U.S.A. 85:7448-7451.

Methods of Treatment

The invention further provides methods of treating subjects having solid malignant or non-malignant tissue mass or tumor selected from rectal cancer, colorectal cancer, (including metastatic CRC), colon cancer, gastric cancer, lung cancer (including non-small cell lung cancer) and esophageal cancer. In one embodiment, the method comprises (a) determining the identity of the allelic variant as identified herein; and (b) administering to the subject an effective amount of a compound or antibody therapy (e.g., Cetuximab antibody, mimetic or biological equivalent thereof) to a patient identified as likely responsive to the therapy based on said screen. This therapy can be combined with other suitable therapies or treatments.

The anti-EGFR antibodies and compositions are administered or delivered in an amount effective to treat the cancer and by any suitable means and with any suitable formulation as a composition and therefore includes a carrier such as a pharmaceutically acceptable carrier. Accordingly, a formulation comprising an antibody or biological equivalent thereof is further provided herein. The formulation can further comprise one or more preservatives or stabilizers. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, and 1.0%).

The antibodies or biological equivalents thereof can be administered as a composition. A "composition" typically intends a combination of the active agent and another carrier, e.g., compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myo-inositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-quadrature-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional proviso that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", 52$^{nd}$ ed., Medical Economics, Montvale, N.J. (1998).

An "effective amount" is an amount sufficient to effect beneficial or desired results. An effective amount can be administered in one or more administrations, applications or dosages.

The invention provides an article of manufacture, comprising packaging material and at least one vial comprising a solution of at least one antibody or its biological equivalent with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising at least one lyophilized antibody or its biological equivalent and a second vial comprising an aqueous diluent of prescribed buffer or preservative, wherein said packaging material comprises a label that instructs a patient to reconstitute the therapeutic in the aqueous diluent to form a solution that can be held over a period of twenty-four hours or greater.

The antibody or equivalent thereof is prepared to a concentration includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

The formulations of the present invention can be prepared by a process which comprises mixing at least one antibody or biological equivalent and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing of the antibody and preservative in an aqueous diluent is carried out using conventional dissolution and mixing procedures. For example, a measured amount of at least one antibody in buffered solution is combined with the desired preservative in a buffered solution in quantities sufficient to provide the antibody and preservative at the desired concentrations. Variations of this process would be recognized by one of skill in the art, e.g., the order the components are added, whether additional additives are used, the temperature and pH at which the formulation is prepared, are all factors that can be optimized for the concentration and means of administration used.

The compositions and formulations can be provided to patients as clear solutions or as dual vials comprising a vial of lyophilized antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available. Recognized devices comprising these single vial systems include pen-injector devices for delivery of a solution such as BD Pens, BD Autojectore, Humaject®, NovoPen®, B-D®Pen, AutoPen®, and Opti-Pen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J. available at bectondickenson.com), Disetronic (Burgdorf, Switzerland, available at disetronic.com; Bioject, Portland, Oreg. (available at bioject.com); National Medical Products, Weston Medical (Peterborough, UK, available at westonmedical.com), Medi-Ject Corp (Minneapolis, Minn., available at mediject.com).

Various delivery systems are known and can be used to administer a therapeutic agent of the invention, e.g., encapsulation in liposomes, microparticles, microcapsules, expression by recombinant cells, receptor-mediated endocytosis. See e.g., Wu and Wu (1987) J. Biol. Chem. 262:4429-4432 for construction of a therapeutic nucleic acid as part of a retroviral or other vector, etc. Methods of delivery include but are not limited to intra-arterial, intra-muscular, intravenous, intranasal and oral routes. In a specific embodiment, it may be desirable to administer the pharmaceutical compositions of the invention locally to the area in need of treatment; this may be achieved by, for example, and not by way of limitation, local infusion during surgery, by injection or by means of a catheter.

The agents identified herein as effective for their intended purpose can be administered to subjects or individuals identified by the methods herein as suitable for the therapy, Therapeutic amounts can be empirically determined and will vary with the pathology being treated, the subject being treated and the efficacy and toxicity of the agent.

Biological Equivalent Antibodies and Therapies

In one aspect, after determining that antibody therapy alone or in combination with other suitable therapy is likely to provide a benefit to the patient, the invention further comprises administration of an anti-EGFR antibody, fragment, variant or derivative thereof. The antibodies of this invention are monoclonal antibodies, although in certain aspects, polyclonal antibodies can be utilized. They also can be functional fragments, antibody derivatives or antibody variants. They can be chimeric, humanized, or totally human. A functional fragment of an antibody includes but is not limited to Fab, Fab', Fab2, Fab'2, and single chain variable regions. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. So long as the fragment or derivative retains specificity of binding or neutralization ability as the antibodies of this invention it can be used. Antibodies can be tested for specificity of binding by comparing binding to appropriate antigen to binding to irrelevant antigen or antigen mixture under a given set of conditions. If the antibody binds to the appropriate antigen at least 2, 5, 7, and preferably 10 times more than to irrelevant antigen or antigen mixture then it is considered to be specific.

The antibodies also are characterized by their ability to specifically bind to an equivalent epitope. The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, which induces the B-lymphocytes to produce IgG immunoglobulins specific for the antigen. This IgG is purified from the mammals serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490 and is herein incorporated by reference in its entirety.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsried/Planegg, Del.), Biovation (Aberdeen, Scotland, UK) Bioinvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1977) Microbiol. Immunol. 41:901-907 (1997); Sandhu et al., (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al., (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol). 17:887-892; Babcook et al., Proc. Natl. Acad. Sci. USA (1996) 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; Kenny et al. (1995) Bio/Technol. 13:787-790); and B-cell selection (Steenbakkers et al. (1994) Molec. Biol. Reports 19:125-134).

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody variant" includes post-translational modification to linear polypeptide sequence of the antibody or fragment. For example, U.S. Pat. No. 6,602,684 B1 describes a method for the generation of modified glycolforms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al., (1998) Plant Mol. Biol. 38:101-109 and reference cited therein. Thus, antibodies of the present invention can also be produced using transgenic plants, according to know methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues are directly and most substantially involved in influencing antigen binding. Humanization or engineering of antibodies of the present invention can be performed using any known method, such as but not limited to those described in U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; and 4,816,567.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. See for example, Russel et al. (2000) Infection and Immunity April: 1820-1826; Gallo et al. (2000) European J. Immun. 30:534-540; Green (1999) J. Immun. Methods 231:11-23; Yang et al. (1999) J. Leukocyte Biology 66:401-410; Yang, X-D (1999) Cancer Research 59(6):1236-1243; Jakobovits (1998) Advanced Drug Delivery Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold, R. (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4): 247-260; Jakobovits (1993) Nature 362(6417):255-258; Jakobovits et al. (1993) Proc. Natl. Acad. Sci. USA 90(6): 2551-2555; Kucherlapati et al. U.S. Pat. No. 6,075,181.

Human monoclonal antibodies can also be produced by a hybridoma which includes a B cell obtained from a transgenic nonhuman animal, e.g., a transgenic mouse, having a genome comprising a human heavy chain transgene and a light chain transgene fused to an immortalized cell.

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (V) connected to a light chain variable domain (V) in the same polypeptide chain (VH V). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.

The term "antibody derivative" further includes "linear antibodies". The procedure for making this is known in the art and described in Zapata et al. (1995) Protein Eng. 8(10): 1057-1062. Briefly, these antibodies comprise a pair of tandem Fd segments (V-C1-VH-C1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen.

If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski, et al. (1985) Proc. Natl. Acad. Sci. USA 82:8653 or Spira, et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn, et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

In some aspects of this invention, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

Antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 ($^{131}$I), yttrium-90 ($^{90}$Y), bismuth-212 ($^{212}$Bi), bismuth-213 ($^{213}$Bi), technetium-99m ($^{99m}$Tc), rhenium-186 ($^{186}$Re), and rhenium-188 ($^{188}$Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin); ribosome inactivating proteins from plants, bacteria and fungi, such as restrictocin (a ribosome inactivating protein produced by *Aspergillus restrictus*), saporin (a ribosome inactivating protein from *Saponaria officinalis*), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

The antibodies for use in this therapy can be further modified. The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis. See generally, Hermanson, G. T. (1996) BIOCONJUGATE TECHNIQUES, Academic Press: San Diego, Calif.

In one aspect of the invention, a biological equivalent of Cetuximab (an anti-EGFR antibody) selected from the group of, but not limited to, Panitumumab (ABX-EGF) as described in US Patent Publ. Nos.: 2005/0272083 and 2004/0033543; TheraCIM, EMD 72000, and MDX447 as described in US Patent Publ. No.: 2007/0014792; or H425 and C225 as described in US Patent Publ. Nos. 2006/0610561, 20050175611, and 2004/0131611, can be used to treat patients identified as having the appropriate genetic polymorphisms.

Also provided is a medicament comprising an effective amount of a therapy as described herein for treatment of a human cancer patient having one or more predictive polymorphisms or genetic markers as identified in Tables 1, 2, 3 or the experimental examples.

Kits

As set forth herein, the invention provides diagnostic methods for determining the type of allelic variant of a polymorphic region present in the gene of interest or the expression level of a gene of interest. In some embodiments, the methods use probes or primers comprising nucleotide sequences which are complementary to the polymorphic region of the gene of interest. Accordingly, the invention provides kits for performing these methods as well as instructions for carrying out the methods of this invention such as collecting tissue and/or performing the screen, and/or analyzing the results, and/or administration of an effective amount of the therapies described above In an embodiment, the invention provides a kit for determining whether a subject responds to cancer treatment or alternatively one of various treatment options. The kits contain one of more of the compositions described above and instructions for use. As an example only, the invention also provides kits for determining response to cancer treatment containing a first and a second oligonucleotide specific for the polymorphic region of the gene. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

The kit can comprise at least one probe or primer which is capable of specifically hybridizing to the polymorphic region of the gene of interest and instructions for use. The kits preferably comprise at least one of the above described nucleic acids. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention. Examples of such assays can be found in Chard (1986) "An Introduction to Radioimmunoassay and Related Techniques" Elsevier Science Publishers, Amsterdam, The Netherlands; Bullock et al., "Techniques in Immunocytochemistry" Academic Press, Orlando, Fla. Vol. 1 (1982), Vol. 2 (1983), Vol. 3 (1985); Tijssen (1985) "Practice and Theory of Immunoassays: Laboratory Techniques in Biochemistry and Molecular Biology", Elsevier Science Publishers, Amsterdam, The Netherlands.

The test samples used in the diagnostic kits include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the gene of interest.

As amenable, these suggested kit components may be packaged in a manner customary for use by those of skill in the art. For example, these suggested kit components may be provided in solution or as a liquid dispersion or the like.
Other Uses for the Nucleic Acids of the Invention The identification of the allele of the gene of interest can also be useful for identifying an individual among other individuals from the same species. For example, DNA sequences can be used as a fingerprint for detection of different individuals within the same species. Thompson and Thompson, eds., (1991) "Genetics in Medicine", W B Saunders Co., Philadelphia, Pa. This is useful, e.g., in forensic studies.

The invention now being generally described, it will be more readily understood by reference to the following examples which are included merely for purposes of illustration of certain aspects and embodiments of the present invention, and are not intended to limit the invention.

EXPERIMENTAL EXAMPLES

Example 1

Background: A phase II study of Cetuximab (IMCL-0144) has shown a response rate of 12% in patients with EGFR expressing metastatic colorectal cancer (mCRC). It was recently reported that polymorphisms in the EGFR pathway may be useful molecular markers to predict clinical outcome. In this larger study, polymorphisms in genes were tested for involvement in the EGFR and whether the angiogenesis pathway will be associated with clinical outcome.

Methods: 136 tissue samples from 346 mCRC patients enrolled in the phase II study of Cetuximab (IMCL-0144) were analyzed and 133 cases were informative. The response rate in these 133 patients was 10% with a median progression-free survival (PFS) of 1.3 months (95% CI, 1.2 to 1.5) and an overall survival time (OS) of 5.5 months (95% CI, 4.1 to 7.5). Gr3-4 toxicity was observed in 56%. Gene polymorphisms of EGFR, Cox-2, EGF, cyclin D1, fragment c γ receptor 2A (FCGR2A), FCGR3A, VEGF, IL-8 were assessed from gDNA extracted from tissue samples by using PCR-based RFLP technique. Univariate analysis (Fisher's exact test for response; A log-rank test for PFS and OS) was performed to examine associations between polymorphisms and clinical outcome. A classification and regression tree (CART) analysis was used to identify subgroups of patients who were more likely to benefit from Cetuximab.

Results: Patients with EGFR G497A G/A, Cox-2 G−765C C/C or EGF A61G G/G genotype showed better PFS (p=0.02, 1.8 mo. vs. 1.2 mo.; p=0.03, 6.9 mo. vs. 1.3 mo.; p=0.04, 1.4 mo. vs. 1.2 mo.), respectively. Trends were noted in associations between Cox-2 and tumor response (p=0.09), between EGF and Grade 3-4 toxicity (FIG. 1, p=0.066). CART analyses indicated that germline polymorphisms in EGFR, EGF, Cox-2, Cyclin D1, IL-8, VEGF, FCGR2A and FCGR3A genes can be used to identify patients who will most likely benefit from Cetuximab therapy. Table 1 describes the genotypes Example 2

In an extension of the experiment described in Example 1, Applicant provides the following Example 2
Materials and Methods:
Patients One hundred and thirty patients with histopathologically confirmed metastatic colorectal carcinoma, who either failed at least two prior chemotherapy regimens or failed adjuvant therapy plus one chemotherapy regimen for metastatic disease, were included in this study. All patients took part in a phase II open-label multicenter study (ImClone-0144) of Cetuximab (C-225), which included a total of 346 patients. All available tissue samples from 130 mCRC patients enrolled were analyzed. The study was performed at the University of Southern California/Norris Comprehensive Cancer Center (USC/NCCC) and was approved by the Institutional Review Board of the University of Southern California for Medical Sciences. All patients provided their written informed consent for tissue and blood collection to allow study of molecular correlates.
Clinical Evaluation of Response Criteria For patients with measurable disease, response was assessed every 6 weeks during the course of the study and criteria were based on modified WHO guidelines. Lenz et al. (2006) J. Clin. Oncol. 24:4914-21. Response to Cetuximab was evaluated retrospectively by an independent response assessment committee that was blinded to the investigator-reported measurements and assessments were reported in the study. Patients underwent weekly blood counts, and physical examinations were performed at every third week.
Genotyping For the experiments repeated above, tissue specimens were collected and genomic DNA was extracted using the QIAamp kit (Qiagen, CA, USA). The majority of the samples were tested using polymerase chain reaction restriction fragment length polymorphism (PCR-RFLP) technique. Briefly, forward and reverse primers were used for PCR amplification, PCR products were digested by restriction enzymes (New England Biolab, Massachussetts, USA) and alleles were separated on 4% NuSieve ethidium bromide stained agarose gel. Forward and reverse primer, restriction enzymes and annealing temperatures are listed in Table 4. If no matching restriction enzyme could be found, samples were analyzed by direct sequencing.

TABLE 4

Primer Sequences, Annealing Temperatures and Restriction Enzymes

| Gene | SEQ ID NO: | Forward-Primer (5'-3') | Reverse-Primer (5'-3') | SEQ ID NO: | Enzyme | Annealing |
|---|---|---|---|---|---|---|
| FCGR2A H131R | 1 | GGAAAATCCCAGAAATTCTCGC | CAACAGCCTGACTACCTATTACGCGGG | 2 | BstUI | 55° |

TABLE 4-continued

Primer Sequences, Annealing Temperatures and Restriction Enzymes

| Gene | SEQ ID NO: | Forward-Primer (5'-3') | Reverse-Primer (5'-3') | SEQ ID NO: | Enzyme | Annealing |
|---|---|---|---|---|---|---|
| FCGR3A V158F | 3 | CTGAAGACACATTTTTACTCCCAAA/C | TCCAAAAGCCACACTCAAAGAC | 4 | n.a. | 64° |
| VEGF C + 936T | 5 | AAGGAAGAGGAGACTCTGCGCAGAGC | TAAATGTATGTATGTGGGTGGGTGTGTCTACAGG | 6 | Nla III | 60° |
| EGF A + 61G | 7 | CATTTGCAAACAGAGGCTCA | TGTGACAGAGCAAGGCAAAG | 8 | Alu I | 60° |
| EGFR (CA)$_n$ repeat | 9 | ACCCCAGGGCTCTATGGGAA | TGAGGGCACAAGAAGCCCCT | 10 | n.a. | 55° |
| EGFR G + 497A | 11 | TGCTGTGACCCACTCTGTCT | CCAGAAGGTTGCACTTGTCC | 12 | Bst-NI | 59° |
| Nrp1 3'UTR C/T | 13 | AGCTTTGGTTGGTTTTGGTG | CCTGGAAACAAAAGGCATTC | 14 | Seq. | 60° |
| IL8 T-251A | 15 | TTGTTCTAACACCTGCCACTCT | GGCAAACCTGAGTCTCACA | 16 | Mfe I | 60° |
| Cox2 T + 8473C | 17 | GTTTGAAATTTTAAAGTACTTTTGAT | TTTCAAATTATTGTTTCATTGC | 18 | BclI | 53° |
| Cox2 G-765C | 19 | ATTCTGGCCATCGCCGCTTC | CTCCTTGTTTCTTGGAAAGAGACG | 20 | Aci I | 55° |
| Cyclin D1 A870G | 21 | GTGAAGTTCATTCCAATCCGC | GGGACATCACCCTCACTTAC | 22 | ScrFI | 61° |

The EGFR(CA)$_n$ repeat polymorphism was determined by a 5'-end 33p γATP labeled PCR protocol with a few modifications. Briefly, the DNA template, dNTPs, 5'-end 33p γATP labeled primer, unlabelled complementary primer, Taq Polymerase (Perkin Elmer Inc, Connecticut, USA) and PCR Buffer were used together in a final PCR. The reaction was carried out and the reaction products were separated on a 6% denaturing polyacrylamide DNA sequencing gel, which then was vacuum blotted for 1 h at 80° C. and exposed to an XAR film (Eastman-Kodak Co. New York, USA) overnight. In addition, the exact number of repeats was confirmed by direct sequencing.

Statistical Analysis

The primary endpoints of this study were progression-free survival (PFS), overall survival (OS), tumor response to Cetuximab, and skin rash toxicity. The progression free survival was calculated from the time of the first date of Cetuximab treatment until the first observation of disease progression or death from any cause. If a patient had not progressed or died, progression-free survival was censored at the time of the last follow up. The overall survival time was calculated as the period from the first day of Cetuximab infusion until death from any cause, or until death from any cause, at which the point data were censored.

The association between each polymorphism with overall survival and progression free survival was analyzed using Kaplan-Meier plots and the log-rank test. The distributions of polymorphisms across demographic characteristics were examined using Fisher's exact test. The associations of each polymorphism with tumor response and toxicity were summarized using contingency tables and the exact conditional test for tumor response and Fisher's exact test for toxicity.

Multivariable analysis was conducted using Cox proportional hazards regression model. A regression tree method based on recursive partitioning (RP) was used to separate patients into homogenous prognostic subgroups for PFS (FIG. 3) by considering gene polymorphisms.

All test of statistical significance were two-sided and no adjustments were made to account for multiple hypothesis testing. Analyses were performed using the SAS statistical package version 9.1 (SAS Institute Inc. Cary, N.C., USA), Epilog Plus Version 1.0 (Epicentre Software, Pasadena, Calif., USA) and RPART function in the S-plus library as described by Therneau and Atkinson (Therneau (1997) Technical Report no. 61, Mayo Clinic, Rochester, Minn.).

Results:

A total of 130 patients with mCRC, refractory to both CPT-11 and oxaliplatin who were treated with single-agent Cetuximab were analyzed. Due to limited tissue sampling, 130 out of 346 (38%) patients were assessable to determine gene polymorphisms. These 130 patients were part of a phase II open-label multicenter study (ImClone 0144) of Cetuximab, which included a total of 346 patients. The patient group has a similar median PFS (1.3 months; 95% CI: 1.3-1.5), OS (5.9 months; 95% CI: 2.7-8.7) and RR (9.2%) compared to the clinical outcome of the entire study population of ImClone 0144 (n=346) which reported a median PFS of 1.4 months (95% CI, 1.4-2.1 months), OS of 6.6 months (95% CI, 5.6-7.6 months) and RR of 11.6% (Lenz et al. (2006) J. Clin. Oncol. 24:4914-21).

There were 121 Caucasian (93%), 1 Hispanic (1%), 3 Asian (2%), 3 African-American (2%) and 2 other (2%) study participants. At the time of analysis, 23 (17%) patients were still alive: the follow-up for those patients ranged from 2.2 to 17.3 month (median follow-up: 12.3 month). Detailed clinicopathologic and demographic characteristics are shown in Table 5.

EGF A+61G Polymorphism and Progression Free Survival

Figure 2:
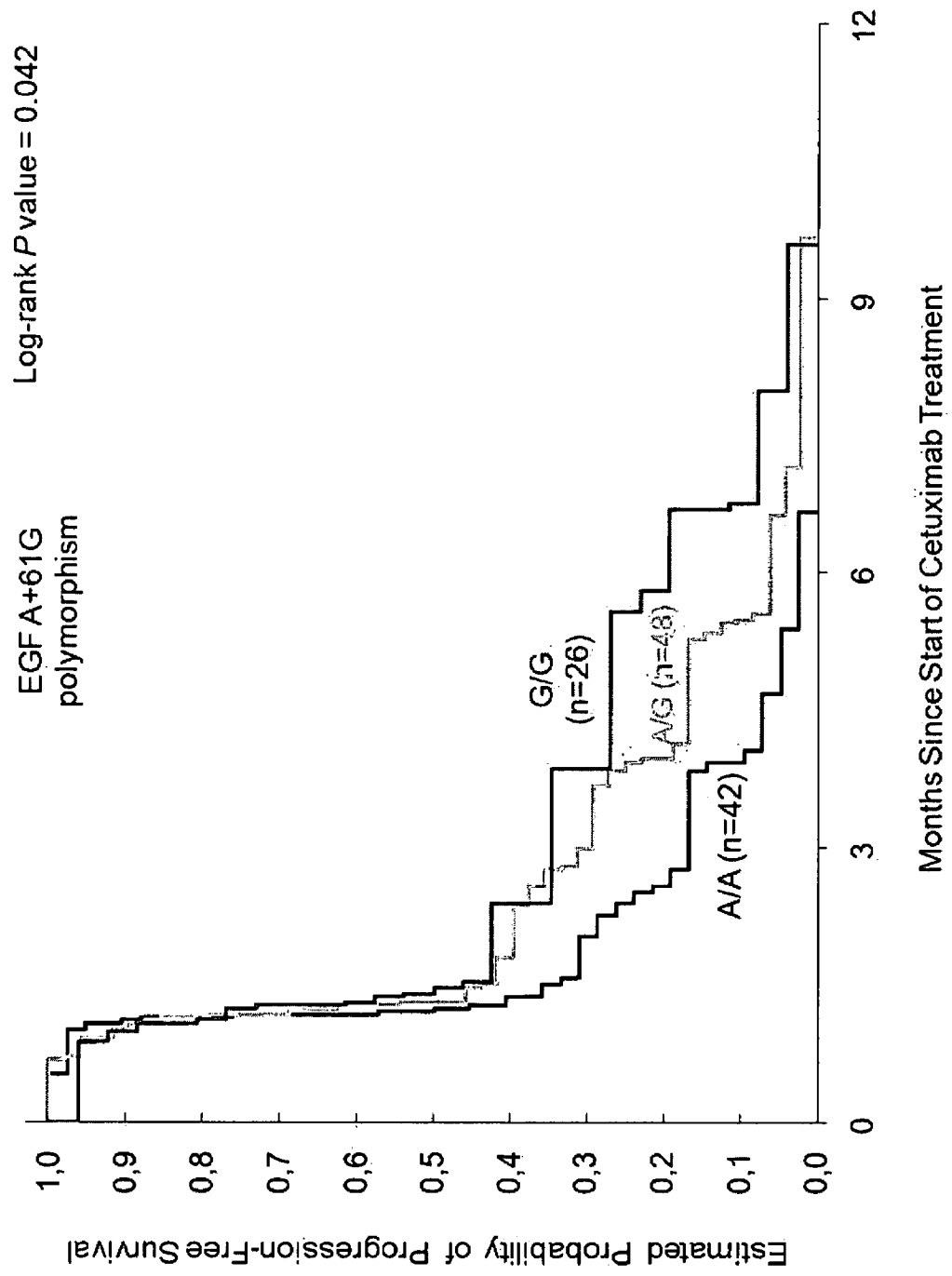
FIG. 2 shows the EGF allele at polymorphism A61G predicts progression free survival (PFS) for mCRC patients treated with Cetuximab. Patients identified as having the genotype G/G show an increase in progression free survival. The letter n equals the number of patients in each group.

Genotyping for EGF A+61G was successful in 116 cases. For 11% of all patients (14/130) genotyping was not successful, because of limited quantity and quality of extracted genomic DNA. EGF A+61G polymorphism showed a significant association with PFS. Patients with the EGF+61G/G homozygous genotype had a median PFS of 1.4 month (95% CI: 1.3 to 3.9 month), compared to 1.2 month (95% CI: 1.2 to 1.5 month), in patients homozygous for the A-allele (p=0.042, log-rank test) (FIG. 2, Table 6).

EGFR G+497A Polymorphism and Progression Free Survival

Figure 3:
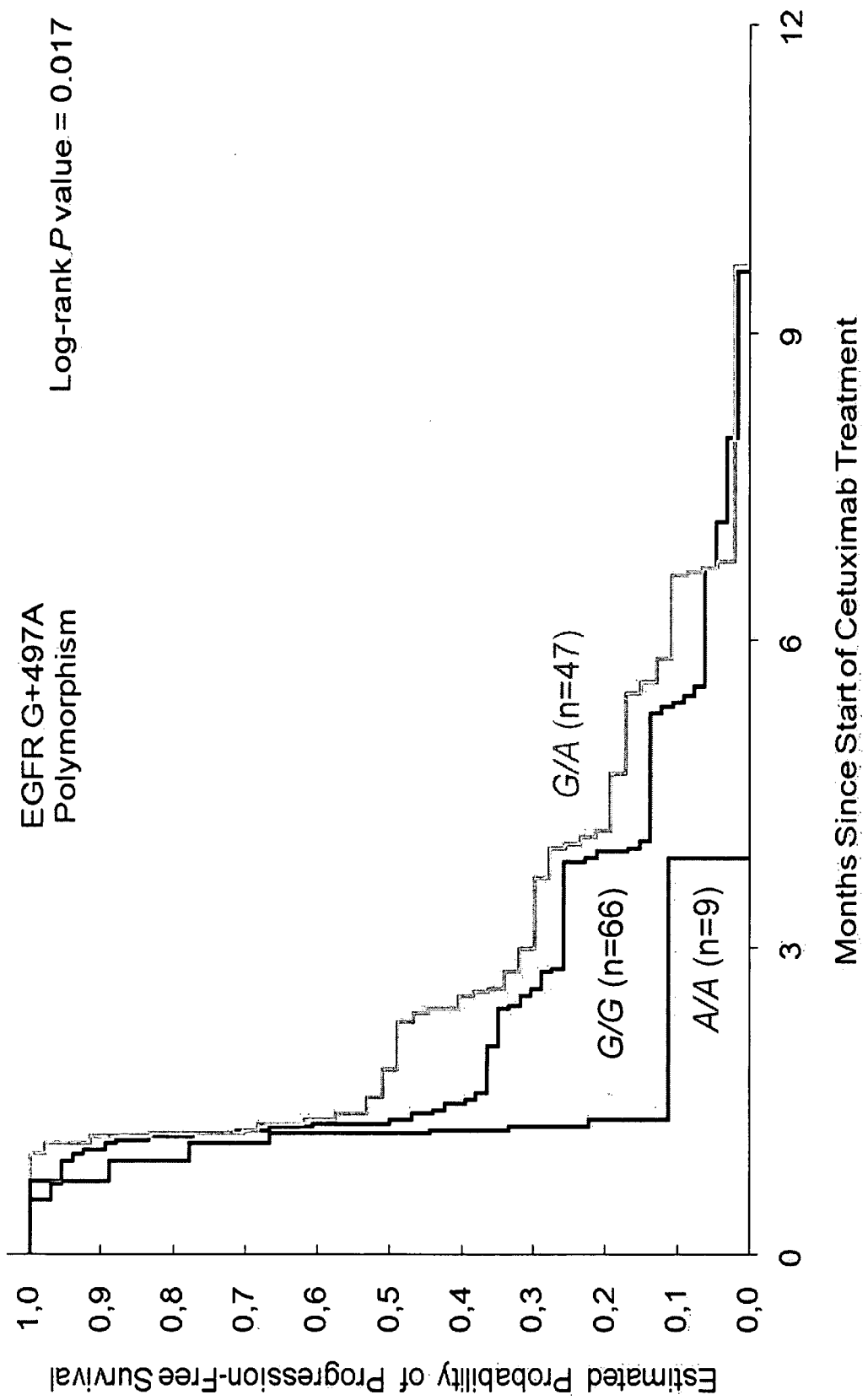
FIG. 3 shows the EGFR allele at polymorphism G497A predicts PFS for mCRC patients treated with Cetuximab. Patients identified as having the genotype G/A show an increase in progression free survival. The letter n equals the number of patients in each group.

Genotyping for EGFR G+497A was successful in 122 cases. For 7% of all patients (9/130) genotyping was not successful, because of limited quantity and quality of extracted genomic DNA. EGFR G+497A polymorphism showed a significant association with PFS. Patients with the EGFR+497 G/G homozygous genotype had a median PFS of 1.3 month (95% CI: 1.2 to 1.5 month), compared to 1.8 month (95% CI: 1.3 to 2.6 month), in patients heterozygous for the A-allele (p=0.017, log-rank test) (FIG. 3, Table 6).

TABLE 5

Baseline Patient Characteristics (n = 130)

| | | Response | | | Skin rash severity | | | Progression-Free Survival | | Overall Survival | |
|---|---|---|---|---|---|---|---|---|---|---|---|
| | N | PR | SD | PD | Grade 0 | Grade 1 | Grade 2-3 | Median, m (95% CI) | Relative Risk (95% CI) | Median, m (95% CI) | Relative Risk (95% CI) |
| Age, years | | | | | | | | | | | |
| ≤54 | 36 | 2 (6%) | 11 (33%) | 20 (61%) | 4 (11%) | 16 (44%) | 16 (44%) | 1.2 (1.2, 1.5) | 1 (Reference) | 5.3 (3.6, 7.5) | 1 (Reference) |
| 54-64 | 45 | 6 (16%) | 12 (32%) | 19 (51%) | 8 (18%) | 21 (47%) | 16 (36%) | 1.4 (1.2, 2.5) | 0.74 (0.48, 1.16) | 7.0 (3.0, 11.5) | 0.69 (0.42, 1.13) |
| ≥65 | 49 | 4 (9%) | 14 (32%) | 26 (59%) | 5 (10%) | 20 (41%) | 24 (49%) | 1.4 (1.3, 2.4) | 0.77 (0.50, 1.19) | 6.6 (3.8, 8.8) | 0.86 (0.54, 1.38) |
| P value | | | 0.87 | | | 0.64 | | 0.34 | | 0.31 | |
| Gender | | | | | | | | | | | |
| Female | 66 | 7 (12%) | 23 (38%) | 30 (50%) | 8 (12%) | 34 (52%) | 24 (36%) | 1.5 (1.3, 2.4) | 1 (Reference) | 7.9 (5.0, 8.9) | 1 (Reference) |
| Male | 64 | 5 (9%) | 14 (26%) | 35 (65%) | 9 (14%) | 23 (36%) | 32 (50%) | 1.3 (1.2, 1.4) | 1.24 (0.88, 1.75) | 4.8 (3.4, 7.0) | 1.34 (0.91, 1.96) |
| P value | | | 0.22 | | | 0.37 | | 0.21 | | 0.13 | |
| ECOG performance status score | | | | | | | | | | | |
| 0 | 52 | 6 (12%) | 19 (39%) | 24 (49%) | 2 (4%) | 19 (37%) | 31 (60%) | 1.4 (1.2, 2.4) | 1 (Reference) | 8.0 (5.3, 12.1) | 1 (Reference) |
| 1 | 76 | 6 (9%) | 18 (28%) | 40 (63%) | 14 (18%) | 37 (49%) | 25 (33%) | 1.3 (1.2, 1.8) | 1.14 (0.80, 1.63) | 4.9 (3.0, 7.0) | 1.79 (1.19, 2.68) |
| P value | | | 0.21 | | | <0.001 | | 0.44 | | 0.003 | |
| Tumor site | | | | | | | | | | | |
| Colon | 99 | 10 (11%) | 26 (30%) | 51 (59%) | 11 (11%) | 45 (45%) | 43 (43%) | 1.3 (1.2, 1.5) | 1 (Reference) | 6.3 (3.8, 8.2) | 1 (Reference) |
| Rectum | 31 | 2 (7%) | 11 (41%) | 14 (52%) | 6 (19%) | 12 (39%) | 13 (42%) | 1.4 (1.2, 2.5) | 1.14 (0.76, 1.72) | 5.5 (3.4, 8.7) | 0.96 (0.61, 1.52) |
| P value | | | 0.87 | | | 0.55 | | 0.51 | | 0.86 | |
| No. of prior chemotherapy regimens | | | | | | | | | | | |
| 2-3 | 58 | 4 (8%) | 16 (30%) | 33 (62%) | 4 (7%) | 31 (53%) | 23 (40%) | 1.3 (1.2, 1.3) | 1 (Reference) | 5.5 (3.6, 7.7) | 1 (Reference) |
| 4-5 | 60 | 6 (12%) | 18 (36%) | 26 (52%) | 11 (18%) | 24 (40%) | 25 (42%) | 1.5 (1.3, 2.6) | 0.79 (0.54, 1.13) | 5.9 (3.7, 8.2) | 1.06 (0.71, 1.58) |
| 6-8 | 12 | 2 (18%) | 3 (27%) | 6 (55%) | 2 (17%) | 2 (17%) | 8 (67%) | 1.4 (1.1, 6.6) | 0.62 (0.33, 1.16) | 12.5 (6.4, 17.7) | 0.60 (0.29, 1.22) |
| P value | | | 0.29 | | | 0.92 | | 0.18 | | 0.26 | |

TABLE 5-continued

Baseline Patient Characteristics (n = 130)

| | N | Response PR | Response SD | Response PD | Skin rash severity Grade 0 | Skin rash severity Grade 1 | Skin rash severity Grade 2-3 | Progression-Free Survival Median, m (95% CI) | Progression-Free Survival Relative Risk (95% CI) | Overall Survival Median, m (95% CI) | Overall Survival Relative Risk (95% CI) |
|---|---|---|---|---|---|---|---|---|---|---|---|
| EGFR tumor immunostaining intensity | | | | | | | | | | | |
| 1+ | 79 | 8 (12%) | 19 (28%) | 41 (60%) | 12 (15%) | 36 (46%) | 31 (39%) | 1.3 (1.2, 1.5) | 1 (Reference) | 5.5 (3.8, 7.7) | 1 (Reference) |
| 2-3+ | 50 | 4 (9%) | 18 (40%) | 23 (51%) | 5 (10%) | 20 (40%) | 25 (50%) | 1.4 (1.3, 2.5) | 0.89 (0.62, 1.27) | 7.3 (3.6, 8.7) | 0.97 (0.65, 1.43) |
| P value | | | 0.67 | | | 0.24 | | 0.51 | | 0.86 | |
| Skin rash severity | | | | | | | | | | | |
| Grade 0-1 | 17 | 0 (0%) | 0 (0%) | 7 (100%) | | | | 1.1 (0.9, 1.3) | 1 (Reference) | 2.0 (1.0, 3.4) | 1 (Reference) |
| Grade 2 | 57 | 6 (11%) | 16 (30%) | 31 (58%) | | | | 1.3 (1.3, 1.5) | 0.37 (0.21, 0.66) | 6.5 (3.6, 8.7) | 0.27 (0.15, 0.48) |
| Grade 3 | 56 | 6 (11%) | 21 (39%) | 27 (50%) | | | | 1.5 (1.2, 2.6) | 0.35 (0.19, 0.61) | 7.6 (5.4, 10.0) | 0.21 (0.12, 0.39) |
| P value | | | 0.087 | | | | | <.0001 | | <.0001 | |

TABLE 6

Genomic Polymorphisms and Clinical Outcome in mCRC Patients Treated with Single Agent Cetuximab

| | N | PR | SD | PD | P value | Grade 0 | Grade 1 | Grade 2-3 | P value | m (95% CI) | Relative Risk (95% CI) | P value | m (95% CI) | Relative Risk (95% CI) | P value |
|---|---|---|---|---|---|---|---|---|---|---|---|---|---|---|---|
| FCGR2A | | | | | 0.93 | | | | 0.72 | | | 0.50 | | | 0.49 |
| H/H | 36 | 2 (6%) | 11 (34%) | 19 (59%) | | 5 (14%) | 14 (40%) | 16 (46%) | | 1.3 (1.2, 1.6) | 1 (Reference) | | 7.5 (3.6, 8.7) | 1 (Reference) | |
| H/R | 29 | 4 (15%) | 8 (31%) | 14 (54%) | | 3 (10%) | 11 (38%) | 15 (52%) | | 1.2 (1.1, 3.9) | 0.76 (0.46, 1.27) | | 5.3 (2.8, 8.7) | 0.73 (0.41, 1.30) | |
| R/R | 37 | 4 (12%) | 9 (26%) | 21 (62%) | | 3 (8%) | 21 (58%) | 12 (33%) | | 1.3 (1.2, 2.5) | 0.91 (0.57, 1.44) | | 5.9 (3.7, 8.6) | 0.92 (0.55, 1.53) | |
| FCGR3A | | | | | 0.85 | | | | 0.13 | | | 0.42 | | | 0.34 |
| F/F | 33 | 3 (11%) | 6 (21%) | 19 (68%) | | 4 (13%) | 10 (31%) | 18 (56%) | | 1.3 (1.2, 1.6) | 1 (Reference) | | 6.4 (3.4, 7.9) | 1 (Reference) | |
| F/V | 58 | 6 (11%) | 21 (38%) | 28 (51%) | | 5 (9%) | 29 (50%) | 24 (41%) | | 1.3 (1.2, 2.5) | 0.84 (0.55, 1.29) | | 6.3 (4.4, 8.7) | 0.71 (0.45, 1.14) | |
| V/V | 38 | 3 (10%) | 9 (29%) | 19 (61%) | | 6 (16%) | 18 (49%) | 13 (35%) | | 1.3 (1.2, 1.5) | 1.08 (0.68, 1.73) | | 4.1 (3.0, 9.3) | 0.87 (0.53, 1.44) | |
| EGFR G497A | | | | | 0.50 | | | | 0.30 | | | 0.017 | | | 0.65 |
| G/G | 66 | 5 (9%) | 20 (36%) | 31 (55%) | | 10 (15%) | 28 (42%) | 28 (42%) | | 1.3 (1.2, 1.5) | 1 (Reference) | | 5.5 (3.6, 7.6) | 1 (Reference) | |
| A/G | 47 | 6 (14%) | 15 (34%) | 23 (52%) | | 4 (9%) | 23 (49%) | 20 (43%) | | 1.8 (1.3, 2.6) | 0.82 (0.56, 1.20) | | 7.3 (4.8, 8.7) | 0.90 (0.59, 1.37) | |

TABLE 6-continued

Genomic Polymorphisms and Clinical Outcome in mCRC Patients Treated with Single Agent Cetuximab

| | N | Response | | | P value | Skin rash severity | | | P value | Progression-Free Survival | | P value | Overall Survival | | P value |
|---|---|---|---|---|---|---|---|---|---|---|---|---|---|---|---|
| | | PR | SD | PD | | Grade 0 | Grade 1 | Grade 2-3 | | Median, m (95% CI) | Relative Risk (95% CI) | | Median, m (95% CI) | Relative Risk (95% CI) | |
| A/A | 9 | 0 (0%) | 1 (13%) | 7 (88%) | | 1 (11%) | 2 (22%) | 6 (67%) | | 1.2 (1.1, 1.2) | 2.16 (1.06, 4.43) | | 2.7 (1.8, 12.1) | 1.30 (0.59, 2.88) | |
| EGFR (CA)$_n$ repeat | | | | | 0.77 | | | | 0.41 | | | 0.73 | | | 0.52 |
| Both repeats <20 | 54 | 6 (13%) | 12 (26%) | 29 (62%) | | 7 (13%) | 20 (37%) | 27 (50%) | | 1.3 (1.2, 1.5) | 1 (Reference) | | 7.0 (4.1, 8.7) | 1 (Reference) | |
| Any repeats ≧20 | 63 | 5 (9%) | 22 (39%) | 30 (53%) | | 7 (11%) | 33 (52%) | 23 (37%) | | 1.3 (1.3, 2.5) | 1.06 (0.73, 1.54) | | 5.5 (3.7, 8.0) | 1.14 (0.76, 1.71) | |
| Cyclin D1 | | | | | 0.60 | | | | 0.36 | | | 0.62 | | | 0.87 |
| G/G | 44 | 2 (5%) | 13 (34%) | 23 (61%) | | 4 (9%) | 19 (43%) | 21 (48%) | | 1.3 (1.2, 1.6) | 1 (Reference) | | 6.5 (3.6, 8.2) | 1 (Reference) | |
| G/A | 48 | 7 (17%) | 10 (24%) | 24 (59%) | | 8 (17%) | 18 (38%) | 22 (46%) | | 1.3 (1.2, 2.3) | 0.85 (0.56, 1.30) | | 5.4 (3.6, 8.7) | 0.92 (0.59, 1.45) | |
| A/A | 34 | 2 (6%) | 13 (41%) | 17 (53%) | | 4 (12%) | 18 (53%) | 12 (35%) | | 1.4 (1.3, 2.8) | 0.82 (0.52, 1.29) | | 5.5 (2.8, 8.6) | 1.05 (0.64, 1.74) | |
| IL-8 T-251A | | | | | 0.32 | | | | 0.004 | | | 0.14 | | | 0.30 |
| A/A | 35 | 3 (12%) | 5 (19%) | 18 (69%) | | 7 (20%) | 19 (54%) | 9 (26%) | | 1.3 (1.2, 1.8) | 1 (Reference) | | 3.4 (2.5, 6.1) | 1 (Reference) | |
| A/T | 63 | 6 (10%) | 19 (33%) | 33 (57%) | | 8 (13%) | 26 (41%) | 29 (46%) | | 1.3 (1.2, 1.5) | 0.81 (0.54, 1.24) | | 6.6 (4.8, 8.2) | 0.85 (0.53, 1.35) | |
| T/T | 30 | 3 (10%) | 12 (41%) | 14 (48%) | | 1 (3%) | 12 (40%) | 17 (57%) | | 1.4 (1.2, 3.9) | 0.63 (0.38, 1.05) | | 8.7 (5.3, 12.0) | 0.66 (0.38, 1.14) | |
| VEGF-936 | | | | | 0.45 | | | | 0.81 | | | 0.87 | | | 0.19 |
| C/C | 89 | 7 (9%) | 25 (32%) | 45 (58%) | | 12 (13%) | 36 (40%) | 41 (46%) | | 1.3 (1.2, 1.6) | 1 (Reference) | | 6.5 (4.9, 8.0) | 1 (Reference) | |
| C/T | 26 | 4 (17%) | 5 (21%) | 15 (63%) | | 3 (12%) | 14 (54%) | 9 (35%) | | 1.3 (1.2, 2.8) | 0.89 (0.58, 1.39) | | 3.4 (2.7, 8.6) | 1.25 (0.77, 2.02) | |
| T/T | 5 | 0 (0%) | 4 (80%) | 1 (20%) | | 0 (0%) | 3 (60%) | 2 (40%) | | 1.3 (1.2, 5.4) | 0.99 (0.40, 2.44) | | 14.5 (1.5, 15.0) | 0.36 (0.09, 1.48) | |
| Cox-2 G-765C | | | | | 0.020 | | | | 0.72 | | | 0.032 | | | 0.48 |
| G/G | 85 | 7 (9%) | 22 (29%) | 46 (61%) | | 9 (11%) | 38 (45%) | 38 (45%) | | 1.3 (1.2, 1.5) | 1 (Reference) | | 5.3 (3.7, 7.9) | 1 (Reference) | |
| G/C | 34 | 2 (7%) | 11 (39%) | 15 (54%) | | 7 (21%) | 15 (44%) | 12 (35%) | | 1.3 (1.2, 2.4) | 1.03 (0.69, 1.54) | | 5.5 (3.4, 10.0) | 0.92 (0.59, 1.43) | |
| C/C | 4 | 3 (75%) | 1 (25%) | 0 (0%) | | 0 (0%) | 1 (25%) | 3 (75%) | | 5.8 (3.8, 9.6) | 0.31 (0.12, 0.84) | | 10.5 (10.1, 13.3) | 0.51 (0.16, 1.61) | |
| Cox2 8473 | | | | | 0.62 | | | | 0.86 | | | 0.003 | | | 0.47 |
| T/T | 58 | 6 (11%) | 18 (34%) | 29 (55%) | | 5 (9%) | 26 (45%) | 27 (47%) | | 1.4 (1.3, 2.6) | 1 (Reference) | | 7.6 (5.0, 8.8) | 1 (Reference) | |
| T/C | 48 | 2 (5%) | 12 (29%) | 28 (67%) | | 9 (19%) | 24 (50%) | 15 (31%) | | 1.3 (1.2, 1.4) | 1.49 (1.01, 2.22) | | 3.8 (2.6, 6.4) | 1.27 (0.83, 1.96) | |
| C/C | 19 | 3 (19%) | 7 (44%) | 6 (38%) | | 2 (11%) | 4 (21%) | 13 (68%) | | 3.8 (1.2, 5.8) | 0.67 (0.40, 1.13) | | 8.7 (3.3, 12.1) | 0.98 (0.55, 1.74) | |
| EGF A61G | | | | | 0.17 | | | | 0.93 | | | 0.042 | | | 0.84 |

TABLE 6-continued

Genomic Polymorphisms and Clinical Outcome in mCRC Patients Treated with Single Agent Cetuximab

| | | Response | | | | Skin rash severity | | | Progression-Free Survival | | | Overall Survival | | |
|---|---|---|---|---|---|---|---|---|---|---|---|---|---|---|
| | N | PR | SD | PD | P value | Grade 0 | Grade 1 | Grade 2-3 | P value | Median, m (95% CI) | Relative Risk (95% CI) | P value | Median, m (95% CI) | Relative Risk (95% CI) | P value |
| A/A | 42 | 2 (6%) | 12 (33%) | 22 (61%) | | 6 (14%) | 18 (43%) | 18 (43%) | | 1.2 (1.2, 1.5) | 1 (Reference) | | 6.4 (3.6, 8.4) | 1 (Reference) | |
| A/G | 48 | 4 (9%) | 14 (32%) | 26 (59%) | | 4 (8%) | 24 (50%) | 20 (42%) | | 1.3 (1.2, 2.6) | 0.72 (0.47, 1.10) | | 5.0 (3.6, 8.7) | 1.13 (0.71, 1.79) | |
| G/G | 26 | 5 (23%) | 6 (27%) | 11 (50%) | | 4 (15%) | 10 (38%) | 12 (46%) | | 1.4 (1.3, 3.9) | 0.57 (0.34, 0.95) | | 5.9 (3.0, 10.5) | 0.99 (0.57, 1.73) | |
| NRP | | | | | 0.48 | | | | 0.21 | | | 0.93 | | | 0.87 |
| C/C | 44 | 4 (10%) | 15 (38%) | 20 (51%) | | 6 (14%) | 21 (48%) | 17 (39%) | | 1.3 (1.2, 2.4) | 1 (Reference) | | 7.3 (5.5, 8.7) | 1 (Reference) | |
| C/T | 51 | 5 (12%) | 13 (30%) | 25 (58%) | | 6 (12%) | 26 (51%) | 19 (37%) | | 1.4 (1.2, 2.4) | 0.98 (0.65, 1.47) | | 4.4 (3.6, 8.6) | 0.91 (0.58, 1.42) | |
| T/T | 32 | 3 (10%) | 8 (27%) | 19 (63%) | | 4 (13%) | 9 (28%) | 19 (59%) | | 1.3 (1.2, 2.4) | 0.92 (0.58, 1.47) | | 5.3 (3.4, 7.5) | 1.02 (0.62, 1.68) | |

Cox-2 G−765C Polymorphism and Progression Free Survival

Figure 4:
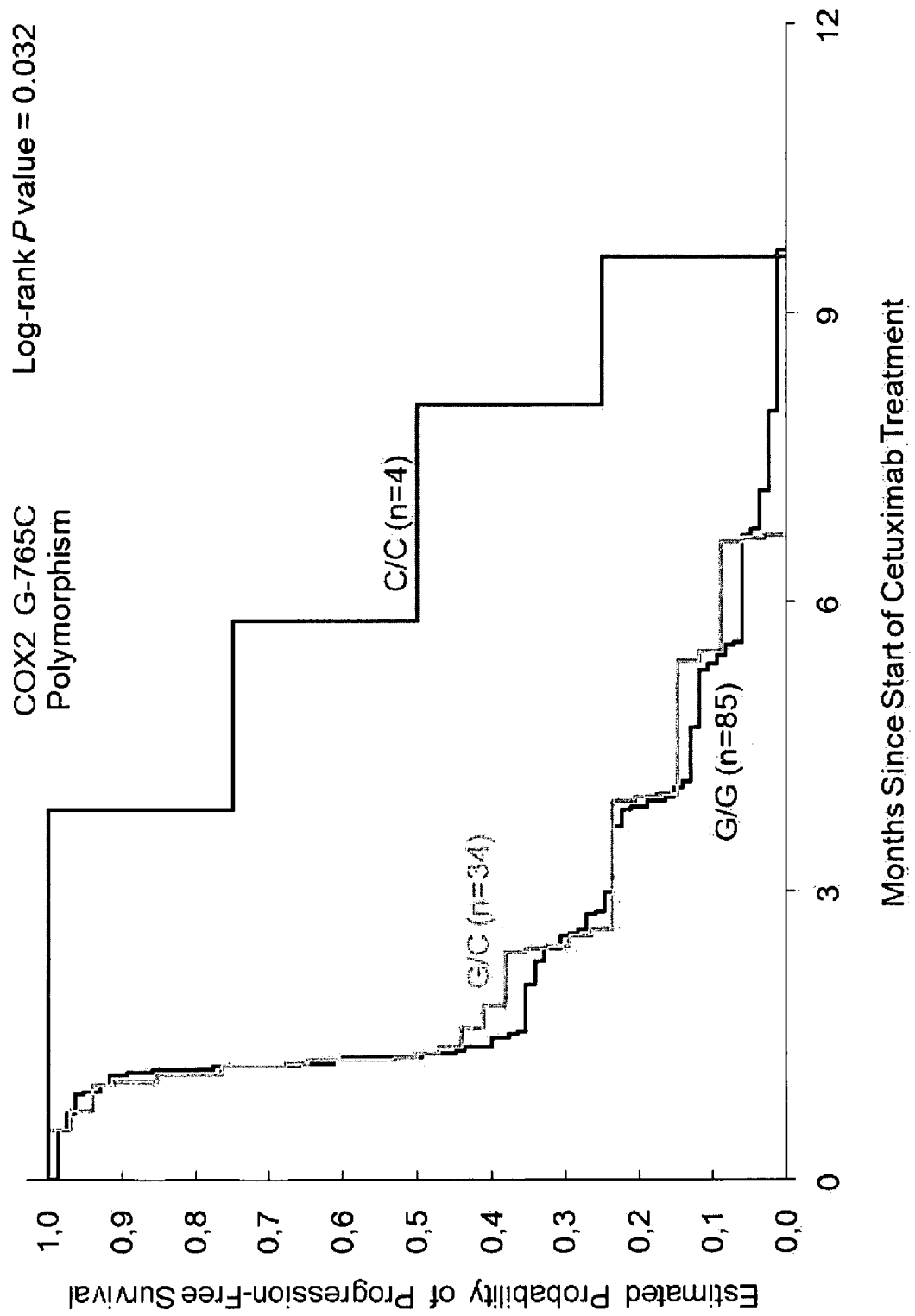
FIG. 4 shows the Cox-2 allele at polymorphism G-765C predicts PFS for mCRC patients treated with Cetuximab. Patients identified as having the genotype C/C show an increase in progression free survival. The letter n equals the number of patients in each group.

Genotyping for Cox-2 G−765C was successful in 123 cases. For 5% of all patients (7/130) genotyping was not successful, because of limited quantity and quality of extracted genomic DNA. Cox-2 G−765C polymorphism showed a significant association with PFS. Patients with the Cox-2−765 G/G homozygous genotype had a median PFS of 1.3 month (95% CI: 1.2 to 1.5 month), compared to 5.8 month (95% CI: 3.8 to 9.6 month), in patients homozygous for the C-allele (p=0.032, log-rank test) (FIG. 4, Table 6).

Cox-2 T+8473C Polymorphism and Progression Free Survival

Figure 5:
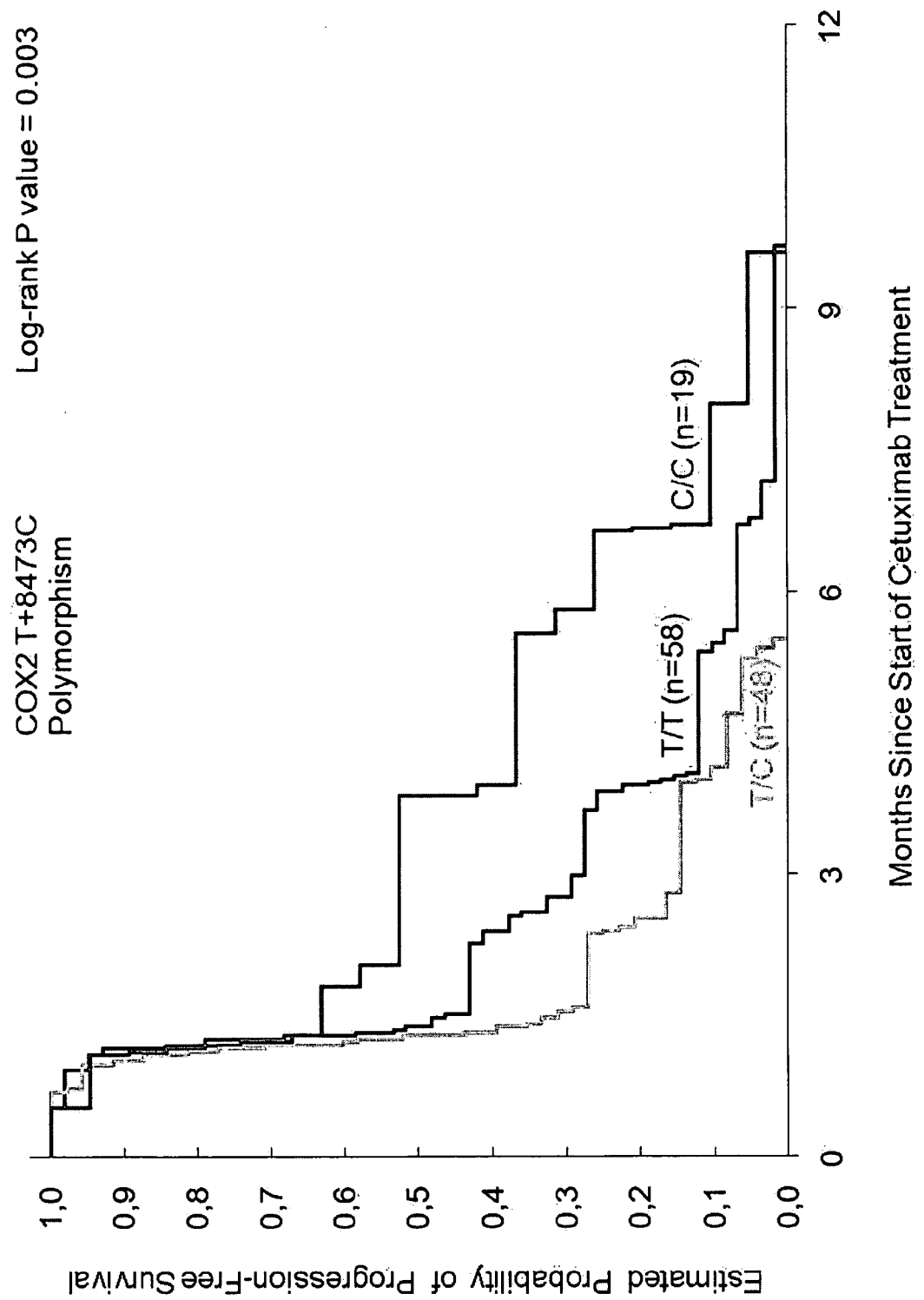
FIG. 5 shows the Cox-2 allele at polymorphism T8473C predicts PFS for mCRC patients treated with Cetuximab. Patients identified as having the genotype C/C show an increase in progression free survival. The letter n equals the number of patients in each group.

Genotyping for Cox-2 T+8473C was successful in 125 cases. For 5% of all patients (6/130) genotyping was not successful, because of limited quantity and quality of extracted genomic DNA. Cox-2 T+8473C polymorphism showed a significant association with PFS. Patients with the Cox-2+8473 T/T homozygous genotype had a median PFS of 1.4 month (95% CI: 1.3 to 2.6 month), compared to 3.8 month (95% CI: 1.2 to 5.8 month), in patients homozygous for the C-allele (p=0.003, log-rank test) (FIG. 5, Table 6).

Gene Polymorphisms and Overall Survival, Response to Cetuximab, and Skin Toxicity Cox-2 G−765C polymorphism showed a significant association with response to Cetuximab. Patients harboring the Cox-2−765 G allele were more likely to experience PD, whereas patients displaying the C allele were more likely to show PR to Cetuximab (p=0.020, log-rank test) (Table 6).

Other tested gene polymorphisms did not show statistically significant associations with overall survival, response to Cetuximab, toxicity and progression free survival (Table 6).

Multivariable Analysis of COX-2 T+8473C, EGF A+61G and EGFR G+497A

When COX-2 T+8473C (adjusted p-value=0.022), EGF A+61G (adjusted p-value=0.040) and EGFR G+497A (adjusted p-value=0.032) were jointly analyzed and stratified by skin rash severity, the three polymorphisms remained significantly associated with clinical outcome (Table 7).

Recursive Partitioning (RP) Analysis of PFS

Figure 6:
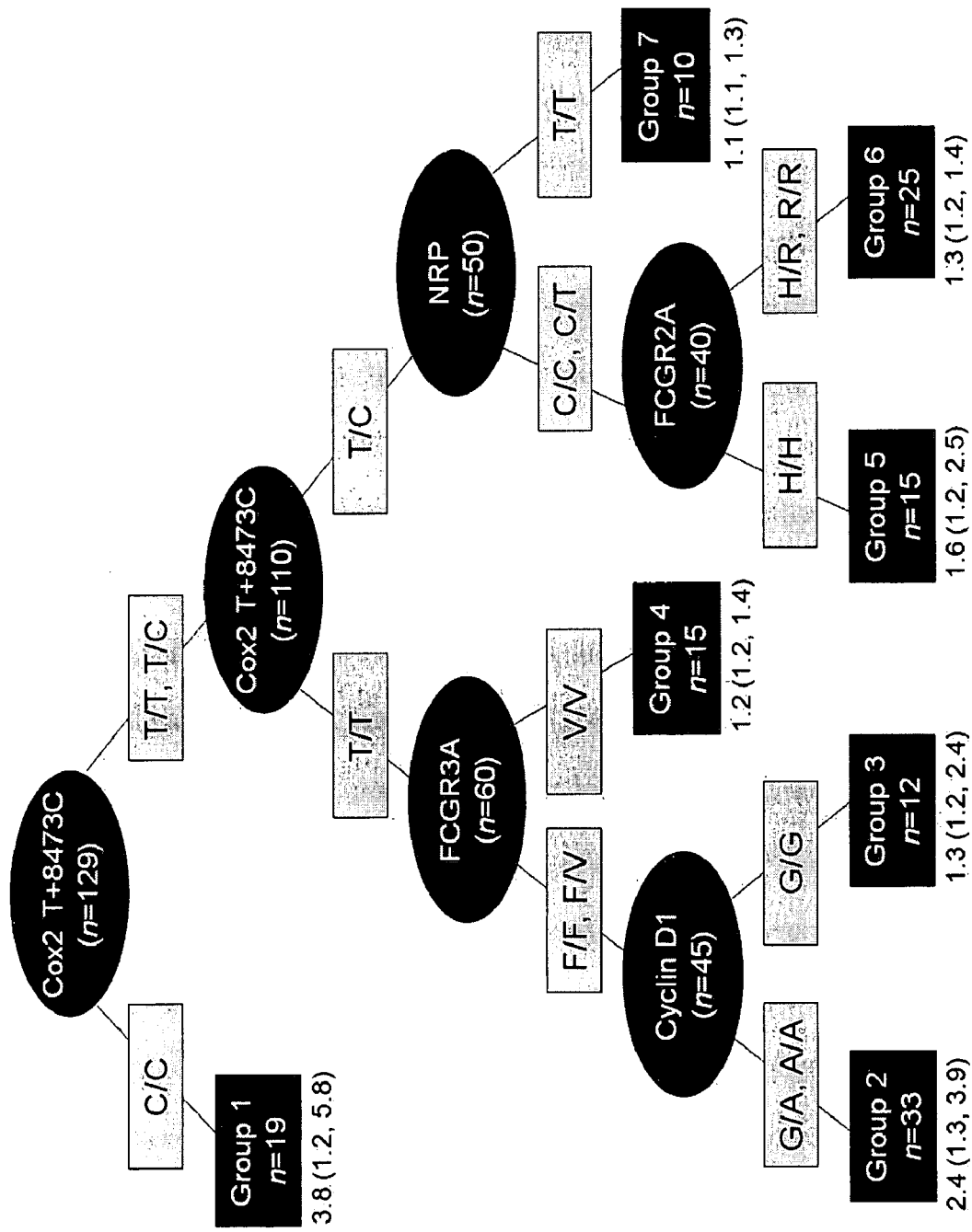
FIG. 6 shows the median PFS (95% confidence interval) using recursive partitioning (RP) analysis for mCRC patients treated with Cetuximab. The letter n equals the number of patients in each group. Square boxes represent terminal nodes, whereas circles represent the parent node and intermediate subgroups.

The 11 genomic polymorphism variables were considered in the RP analysis. The classification tree for PFS is shown in FIG. 3. The first split was based on COX-2 T+8473C polymorphism. For patients with COX-2+8473 C/C genotype no further subgroups could be identified. Among those with +8473 T/C or T/T, further splits were made with FCGR3A, NRP, Cyclin D1 and FCGR2A polymorphisms. Seven terminal nodes were fit. The high-risk groups (short PFS) included group 3, group 4, group 6 and group 7. The favorable prognostic groups (long PFS) included group 1, group 2 and group 5 (FIG. 6).

TABLE 7

Multivariable Analysis of COX-2, EGF and EGFR Polymorphisms and PFS

| | N* | Adjusted RR (95% CI)† | Adjusted P value† |
|---|---|---|---|
| EGFR G497A | | | 0.032 |
| G/G | 60 | 1 (Reference) | |
| A/G | 43 | 0.77 (0.51, 1.16) | |
| A/A | 8 | 2.50 (1.14, 5.46) | |
| COX2 8473 | | | 0.022 |
| T/T | 50 | 1 (Reference) | |
| T/C | 43 | 1.50 (0.92, 2.44) | |
| C/C | 18 | 0.61 (0.34, 1.08) | |
| EGF A61G | | | 0.040 |
| A/A | 39 | 1 (Reference) | |
| A/G | 48 | 0.74 (0.47, 1.15) | |
| G/G | 24 | 0.48 (0.27, 0.86) | |

*Patients with missing EGFR G497A, COX2 8473, or EGF A61G were excluded.
†Based on COX proportional hazards model, stratified by skin rash severity, with all three gene polymorphisms included Discussion:

These experiments were able to demonstrate that germline polymorphisms of genes involved in the EGF/EGFR signaling pathway are independently associated with clinical outcome in patients with mCRC treated with single agent Cetuximab. To the best of the Applicant's knowledge, this is the first study to show, that polymorphisms in COX-2, EGF and EGFR may be important prognostic and predictive markers, independently of skin-rash severity in this patient population.

EGFR targeted therapy with Cetuximab has shown promising results in multiple phase II clinical trials. Saltz et al., Cunningham et al. and Lenz et al. reported response rates of 9.0%, 10.8% and 11.6% respectively, for patients with mCRC treated with Cetuximab either alone or in combination with CPT-11 (Cunningham et al. (2004) N. Engl. J. Med. 351:337-45; Saltz et al. (2004) J. Clin. Oncol. 22:1201-8; Lenz et al. (2006) J. Clin. Oncol. 24:4914-21). All trials have so far failed to show a significant correlation between EGFR expression, determined by immunohistochemistry and clinical outcome. In fact, antitumor activity of Cetuximab was also noted in patients, whose tumors were negative for EGFR immunostaining (Lenz et al. (2006) J. Clin. Oncol. 24:4914-21).

Cyclooxygenase (COX) is the rate-limiting enzyme in the conversion of arachidonic acid to prostaglandins. The isoform COX-1 is thought to be constitutively expressed in a variety of tissues, whereas COX-2 is induced by cytokines, growth factors, mitogens and oncoproteins (Stoehlmacher and Lenz (2003) Semin. Oncol. 30:10-6). COX-2 is involved in the regulation of a broad range of cellular processes including tumor onset and progression, metastases, angiogenesis, and resistance to chemotherapy (Dandekar and Lokeshwar (2004) Clin. Cancer Res. 10:8037-47; Kishi et al. (2000) Cancer Res. 60:1326-31; Oshima et al. (1996) Cell 87:803-9; Tsujii et al. (1997) Proc. Natl. Acad. Sci. USA 94:3336-40; Tsujii et al. (1998) Cell 93:705-16). In fact, overexpression of COX-2 has been reported in a variety of malignancies, including colorectal carcinoma (Buskens et al., (2003) Scand. J. Gastroenterol. Suppl. (239):87-93; Funkhouser and Sharp (1995) Cancer 76:1116-9; van Rees and Ristimaki (2001) Scand. J. Gastroenterol. 36:897-903; Lurje et al. (2007) J. Gastrointest. Surg. 11(9):1105-1111). The relationship between COX-2 and the EGF/EGFR signalling pathway is still controversial (Dannenberg et al. (2005) J. Clin. Oncol. 23:254-66). COX-2 is thought to be a downstream effector of EGFR and was found to be induced by EGF-mediated stimulation of EGFR tyrosine kinase in human glioma cell lines (Xu and Shu (2007) Cancer Res. 67:6121-9). In vivo models by Xu et al. showed that COX-2 expression is strongly induced by p38 mitogen activated protein kinase mediated EGF stimulation (Xu and Shu (2007) Cancer Res. 67:6121-9). Other studies demonstrated that COX-2 may be an upstream effector of EGFR in human colon cancer cells lines, suggesting that COX-2 induces colon cancer carcinogenesis by the activation of EGFR (Kinoshita et al. (1999) Biochim. Biophys. Acta. 1438:120-30; Pai et al. (2002) Nat. Med. 8:289-93). Furthermore, COX-2 has been reported to be a predictive and prognostic factor in a variety of malignancies (Vallbohmer et al. (2005) J. Clin. Oncol. 23:3536-44; Dandekar and Lokeshwar (2004) Clin. Cancer Res. 10:8037-47; Kishi et al. (2000) Cancer Res. 60:1326-31). In fact, high expression levels of COX-2 are known to be associated with shorter OS in ovarian, head and neck cancer and colorectal cancer (Vallbohmer et al. (2005) J. Clin. Oncol. 23:3536-44; Denkert et al. (2002) Am. J. Pathol. 160:893-903; Gallo et al. (2002) Hum. Pathol. 33:708-14). COX-2 G−765C is a frequent single nucleotide polymorphism (SNP) and is located 765 base pairs upstream of the COX-2 transcription start site. The −765C allele was shown to be associated with significantly lower COX-2 promoter activity and associate lower C-reactive protein (CRP) plasma levels compared to the −765G variant (Papafili et al. (2002) Arterioscler. Thromb. Vasc. Biol. 22:1631-6). Other common variants within the COX-2 gene include the COX-2 T+8473C SNP. The COX-2 T+8473C polymorphism is located within the functional region of 3'UTR of the gene, and therefore, may have a potential functional relevance in carcinogenesis, perhaps through the control of stability or degradation of the mRNA (Cok and Morrison (2001) J. Biol. Chem. 276:23179-85; Hu et al. (2005) Lung Cancer 48:11-7). The +8473C allele was significantly less common in patients with lung cancer compared to healthy control patients, suggesting a protective effect against lung cancer (Hu et al. (2005) Lung Cancer 48:11-7). The present study found "low-expression" variants of COX-2 (COX-2−765C and COX-2+8473C) to be significantly associated with higher PFS in both univariate and multivariable analysis (Table 6 and Table 7). These findings are therefore consistent with previous reports, demonstrating that COX-2 mRNA overexpression is a prognostic marker in mCRC (Vallbohmer et al. (2005) J. Clin. Oncol. 23:3536-44). In addition, patients displaying the COX-2−765 C/C genotype were more likely to experience PR to Cetuximab, compared to patients harboring the −765 A allele (log-rank test; p=0.02) (Table 6), suggesting that COX-2 may be a prognostic and predictive marker for mCRC patients treated with single agent Cetuximab.

EGFR, a member of the type I receptor tyrosine kinase family, is known to be overexpressed in a variety of malignancies, including up to 77% of CRC patients and is associated with tumor progression and poor clinical outcome (Salomon et al. (1995) Crit. Rev. Oncol. Hematol. 19:183-232; Hemming et al. (1992) J. Surg. Oncol. 51:147-52). Several in vitro studies have reported functional polymorphisms in genes within the EGFR pathway. There are two functionally significant polymorphisms within the EGFR gene. EGFR G+497A is a SNP in codon 497, which has been associated with an arginine (arg)→lysine (lys) substitution in the extracellular domain within subdomain IV. Moriai et al. were able to show, that the lys/lys genotype confers an attenuated function in EGFR ligand binding, growth stimulation, tyrosine kinase activation and induction of proto-oncogenes (Moriai et al. (1994) Proc. Natl. Acad. Sci. USA 91:10217-21). A second functional polymorphism within the EGFR gene is a highly polymorphic CA repeat within intron 1. The length of this $(CA)_n$ dinucleotide repeat correlates inversely the transcriptional activity of the EGFR gene in vitro and in vivo (Buerger et al. (2000) Cancer Res. 60:854-7; Gebhardt et al. (1999) J. Biol. Chem. 274:13176-80). EGF A+61G is a SNP located in the 5'-UTR region of the epidermal growth factor (EGF) gene, which is one of the natural ligands of EGFR. EGF A+61G alters RNA stability and is associated with EGF plasma levels (Bhowmick et al. (2004) Cancer Res. 64:1220-3). To date, EGF and EGFR polymorphisms have not been reported to be independently associated with PFS in mCRC patients treated with single-agent Cetuximab. In this study, EGF A+61G and EGFR G+497A were found to be significantly associated with PFS in both univariate and multivariable analysis (Table 6 and Table 7).

It was previously reported that Cyclin D1, FCGR2A and FCGR3A are associated with OS and PFS in the same study population as this study. In this larger and multicenter prospective phase II clinical trial, the results of the presented study could not validate these prior results which used univariate analysis. However, CART analyses indicated that germline polymorphisms in EGFR, EGF, COX-2, Cyclin D1, IL-8, FCGR2A and FCGR3A genes could be used to identify patients who will most likely benefit from Cetuximab therapy. In summary COX-2−765 C/C (p=0.03), COX-2+

8473 C/C (p=0.003), EGF+61 G/G (p=0.04) and EGFR+497 G/A (p=0.02) have been identified as independent molecular markers for PFS in mCRC patients treated with single agent Cetuximab. To the best of the Applicants knowledge, this is the first study to show that polymorphisms in COX-2, EGF and EGFR predict clinical outcome in mCRC patients treated with single agent Cetuximab, independently of skin-rash severity. These results confirm previous reports and shows that polymorphisms in COX-2, EGF and EGFR may serve as prognostic and predictive markers in this study population.

Furthermore, these result will not only help us to identify patients who are at high risk, but they will also be critical in selecting more efficient treatment strategies.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A method for determining whether a human colorectal cancer patient is likely or less likely responsive to a single agent anti-EGFR antibody based therapy selected from Cetuximab or an antibody that binds to the same epitope that Cetuximab binds, comprising screening a suitable cell or tissue sample isolated from said patient for the genetic polymorphism of COX-2 T8473C SNP wherein the presence of the genetic polymorphism of (C/C) for COX-2 T8473C SNP indicates the patient is likely responsive to said single agent anti-EGFR antibody based therapy and wherein the absence of the genetic polymorphism of (C/C) for COX-2 T8473C SNP indicates the patient is less likely responsive to said single agent anti-EGFR antibody based therapy.

2. The method of claim 1, wherein the colorectal cancer is a metastatic or non-metastatic cancer selected from the group consisting of rectal cancer, colorectal cancer, and colon cancer.

3. The method of claim 1, wherein the patient is suffering from metastatic colorectal cancer.

4. The method of claim 1, wherein the presence of the genetic polymorphism of (C/C) for COX-2 T8473C SNP indicates the patient is likely responsive to said single agent anti-EGFR antibody based therapy.

5. The method of claim 1, wherein the absence of the genetic polymorphism of (C/C) for COX-2 T8473C SNP indicates the patient is less likely responsive to said single agent anti-EGFR antibody based therapy.

* * * * *